United States Patent
Harrison et al.

(10) Patent No.: US 11,284,878 B2
(45) Date of Patent: Mar. 29, 2022

(54) SUTURE CUTTER

(71) Applicant: Anchor Orthopedics XT Inc., Mississauga (CA)

(72) Inventors: Robert Harrison, Milton (CA); Andrew Oldham, Etobicoke (CA); Ilinca Popovici, Toronto (CA); Neil Godara, Milton (CA); Jeffery Arnett, Gilbert, AZ (US); Aye Nyein San, Mississauga (CA)

(73) Assignee: Anchor Orthopedics XT Inc., Mississauga (CA)

( * ) Notice: Subject to any disclaimer, the term of this patent is extended or adjusted under 35 U.S.C. 154(b) by 763 days.

(21) Appl. No.: 14/913,230

(22) PCT Filed: Aug. 22, 2014

(86) PCT No.: PCT/IB2014/064030
§ 371 (c)(1),
(2) Date: Feb. 19, 2016

(87) PCT Pub. No.: WO2015/025301
PCT Pub. Date: Feb. 26, 2015

(65) Prior Publication Data
US 2016/0199056 A1    Jul. 14, 2016

Related U.S. Application Data

(60) Provisional application No. 61/868,910, filed on Aug. 22, 2013.

(51) Int. Cl.
*A61B 17/04* (2006.01)
*A61B 17/00* (2006.01)

(52) U.S. Cl.
CPC .. *A61B 17/0467* (2013.01); *A61B 2017/0046* (2013.01)

(58) Field of Classification Search
CPC ............ A61B 17/0467; A61B 17/0469; A61B 17/0483; A61B 2017/00353;
(Continued)

(56) References Cited

U.S. PATENT DOCUMENTS 3,372,477 A * 3/1968 Hoppe ............... A61B 17/0467
606/138
3,672,054 A * 6/1972 Kaufman ........... A61B 17/3201
30/294

(Continued)

FOREIGN PATENT DOCUMENTS

| JP | 2006518261 | 8/2006 |
| WO | 1998012970 A1 | 4/1998 |

OTHER PUBLICATIONS

Corresponding Japanese Application, Office Action, dated Jun. 5, 2018.
(Continued)

*Primary Examiner* — Dianne Dornbusch
(74) *Attorney, Agent, or Firm* — Nir Lifshitz

(57) ABSTRACT

A method and apparatus are disclosed for cutting a strand of suture. The apparatus comprises a solid outer member defining a lumen there-through. An inner member is received at least partially within the lumen, a portion of the inner member defining a curve. The inner member further defines a feature for retaining a strand of suture. At least one of the inner and outer members are moveable with respect to the other of the inner and outer members for cutting the strand of suture.

21 Claims, 27 Drawing Sheets

(58) Field of Classification Search
CPC .. A61B 2017/0046; A61B 2017/00738; A61B 2017/00862; A61B 2017/00991; A61B 2017/0474; A61B 2017/2904; A61B 2017/2905; A61B 17/0482

See application file for complete search history.

(56) References Cited

U.S. PATENT DOCUMENTS

| | | | | |
|---|---|---|---|---|
| 3,995,619 | A * | 12/1976 | Glatzer | A61B 10/0275 600/550 |
| 5,176,691 | A * | 1/1993 | Pierce | A61B 17/0469 606/144 |
| 5,452,513 | A * | 9/1995 | Zinnbauer | A61B 17/0467 30/124 |
| 5,499,991 | A * | 3/1996 | Garman | A61B 17/0483 606/148 |
| 5,549,618 | A * | 8/1996 | Fleenor | A61B 17/0469 112/169 |
| 5,649,939 | A * | 7/1997 | Reddick | A61B 17/0469 606/148 |
| 5,755,730 | A * | 5/1998 | Swain | A61B 17/0467 606/148 |
| 7,491,212 | B2 * | 2/2009 | Sikora | A61B 17/0467 606/148 |
| 7,879,055 | B1 * | 2/2011 | Stone | A61B 17/0482 606/170 |
| 8,597,307 | B2 * | 12/2013 | Miller | A61B 17/0467 606/138 |
| 8,603,125 | B2 * | 12/2013 | Stone | A61B 17/0467 606/138 |
| 8,834,497 | B2 * | 9/2014 | Snell | A61B 17/0467 606/148 |
| 8,911,457 | B2 * | 12/2014 | Koogle, Jr. | A61B 17/0467 606/148 |
| 2003/0120287 | A1 * | 6/2003 | Gross | A61B 17/0467 606/148 |
| 2003/0181926 | A1 * | 9/2003 | Dana | A61B 17/0467 606/148 |
| 2004/0097865 | A1 * | 5/2004 | Anderson | A61B 17/0485 604/22 |
| 2004/0122450 | A1 * | 6/2004 | Oren | A61B 17/0483 606/148 |
| 2004/0162569 | A1 * | 8/2004 | Sikora | A61B 17/0483 606/148 |
| 2004/0254598 | A1 * | 12/2004 | Schumacher | A61B 17/0467 606/170 |
| 2005/0038449 | A1 | 2/2005 | Sancoff et al. | |
| 2005/0059983 | A1 * | 3/2005 | Opolski | A61B 17/0467 606/148 |
| 2005/0234481 | A1 * | 10/2005 | Waller | A61B 17/0467 606/148 |
| 2005/0277957 | A1 * | 12/2005 | Kuhns | A61B 17/0401 606/148 |
| 2006/0178682 | A1 * | 8/2006 | Boehlke | A61B 17/0057 606/148 |
| 2006/0293700 | A1 * | 12/2006 | Dana | A61B 17/0467 606/148 |
| 2007/0005081 | A1 * | 1/2007 | Findlay, III | A61B 17/0467 606/148 |
| 2007/0106310 | A1 | 5/2007 | Goldin et al. | |
| 2007/0173865 | A1 * | 7/2007 | Oren | A61B 17/0467 606/148 |
| 2009/0005792 | A1 * | 1/2009 | Miyamoto | A61B 17/0487 606/139 |
| 2009/0088778 | A1 * | 4/2009 | Miyamoto | A61B 17/12013 606/144 |
| 2009/0228026 | A1 * | 9/2009 | Koogle, Jr. | A61B 17/0467 606/148 |
| 2011/0029012 | A1 * | 2/2011 | Tegels | A61B 17/0057 606/213 |
| 2012/0109156 | A1 * | 5/2012 | Overes | A61B 17/0057 606/139 |
| 2012/0136378 | A1 * | 5/2012 | Snell | A61B 17/0467 606/148 |
| 2013/0231701 | A1 * | 9/2013 | Voss | A61B 17/0057 606/232 |
| 2015/0088163 | A1 * | 3/2015 | George | A61B 17/0469 606/138 |
| 2017/0007259 | A1 * | 1/2017 | Kimura | A61B 17/0467 |

OTHER PUBLICATIONS

Corresponding Japanese Application, Office Action, dated Feb. 12, 2019.
Corresponding European Application, European Search Opinion, dated Mar. 7, 2017.
Corresponding European Application, European Search Report, dated Mar. 7, 2017.
Corresponding European Application, Office Action, dated Jan. 31, 2018.
Corresponding European Application, European Search Report, dated Nov. 3, 2020.
Corresponding European Application, European Search Opinion, dated Nov. 3, 2020.
Corresponding European Application, Office Action, dated Aug. 3, 2021.
Corresponding Japanese Application, Office Action, dated Sep. 8, 2020.
Corresponding Canadian Application, Office Action, dated Sep. 16, 2020.
Corresponding Canadian Application, Office Action, dated Mar. 26, 2021.
Corresponding Canadian Application, Office Action, dated Sep. 22, 2021.
Corresponding Patent Corporation Treaty Application, International Search Report, dated Dec. 3, 2014.

* cited by examiner

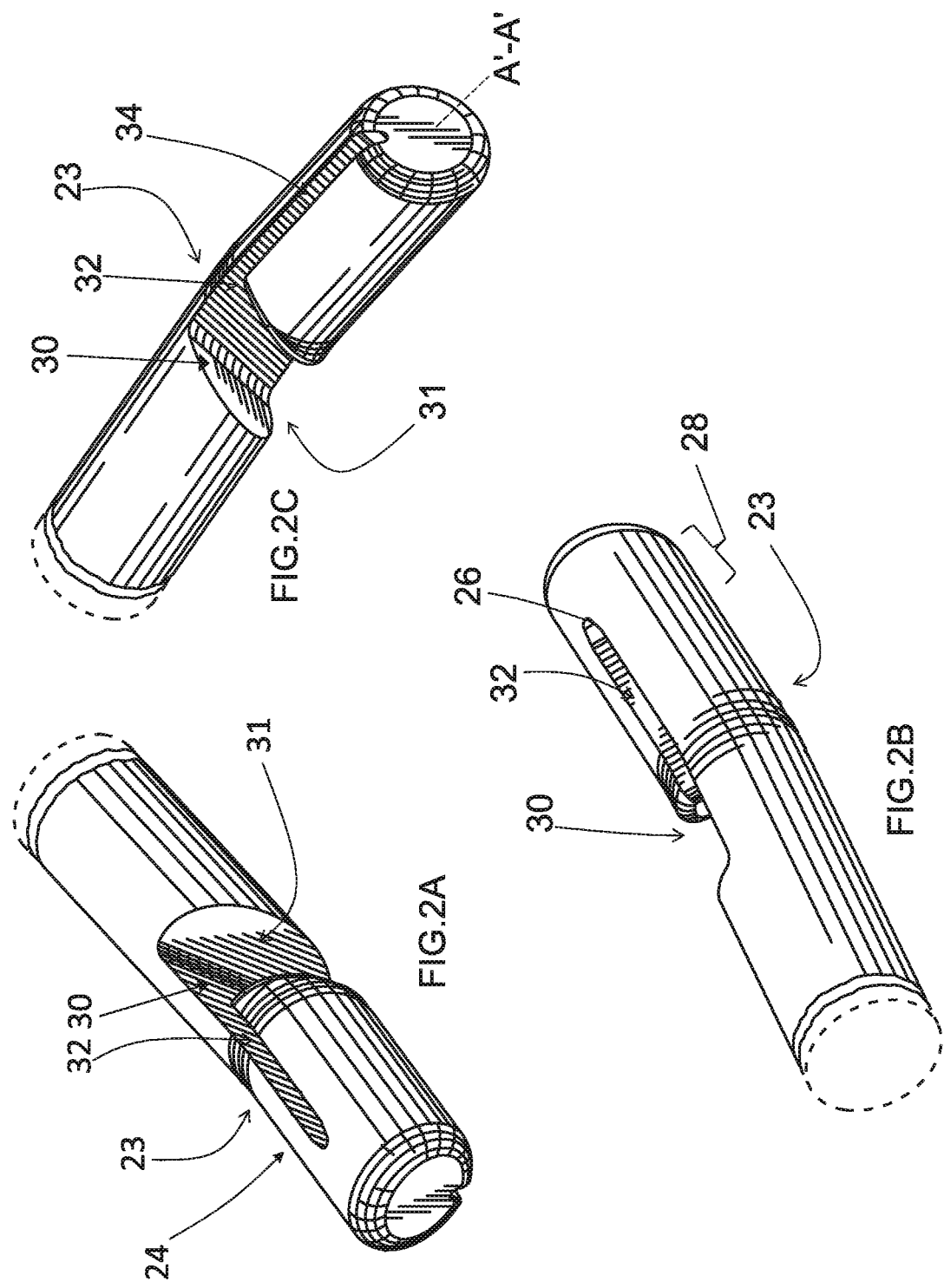

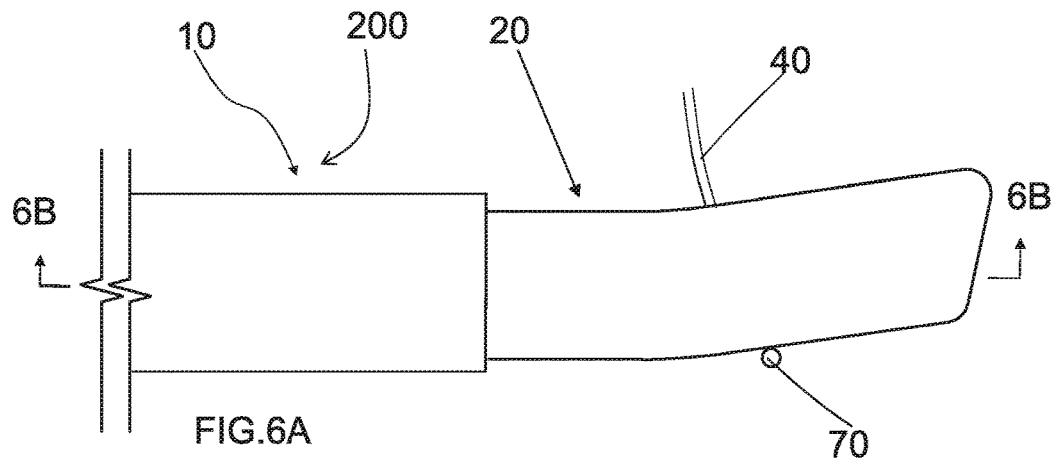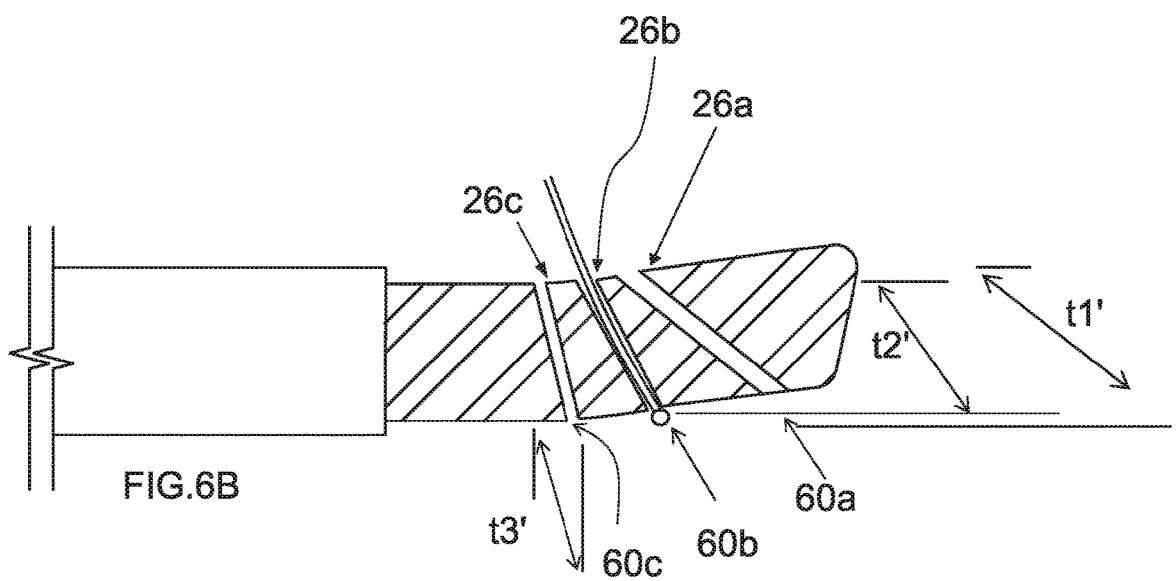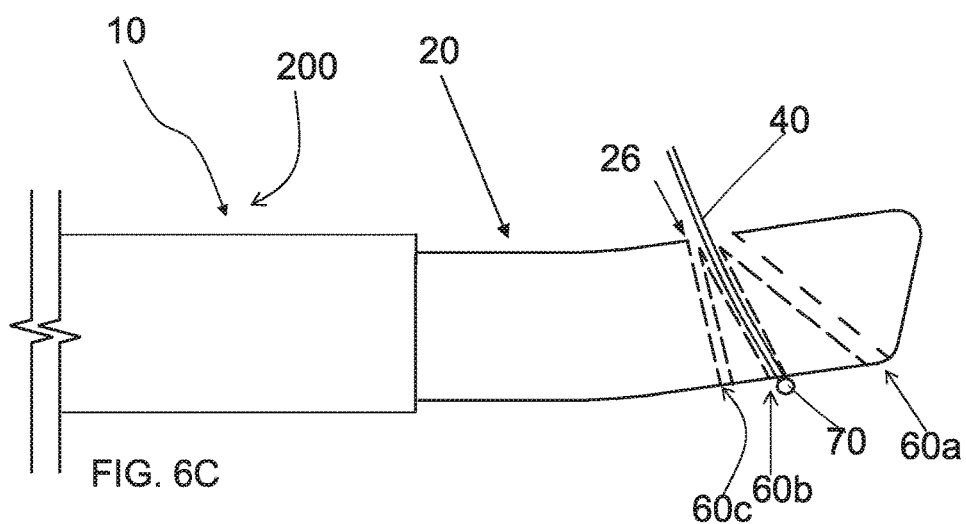

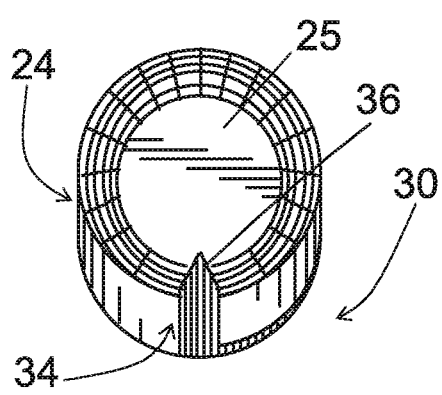
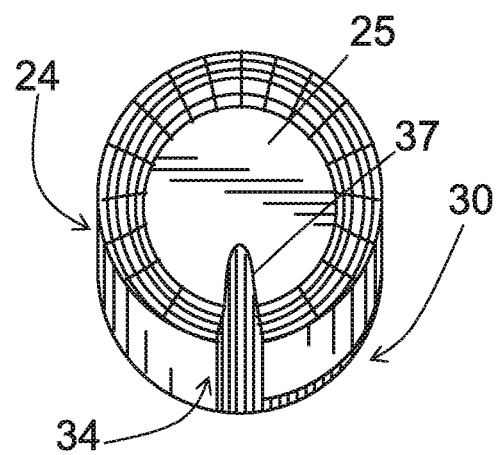
FIG.8A  FIG.8B
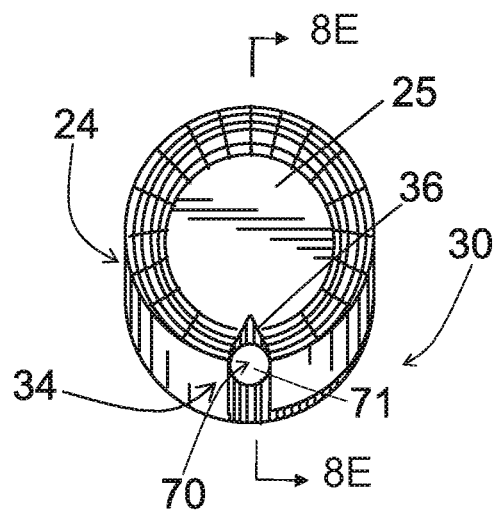
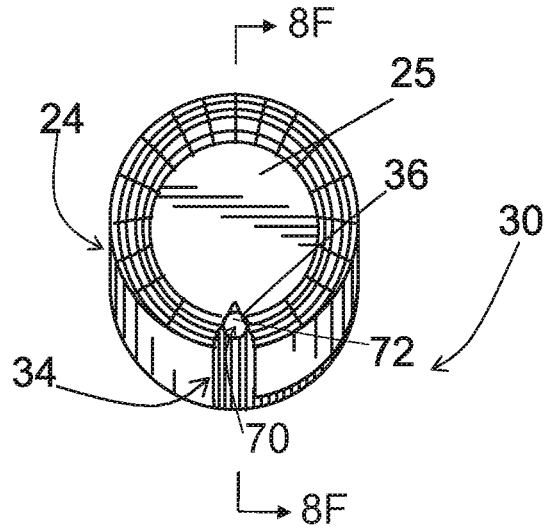
FIG.8C  FIG.8D

SUTURE CUTTER

TECHNICAL FIELD

The disclosure relates to medical devices. More specifically, this disclosure relates to a suture cutter.

BACKGROUND OF THE ART

US Patent Publication US 2004/0162569A1 to Sikora discloses a suture cutter having a curved inner member and an outer member that is moveable along the curved inner member. The outer member has a flexible portion which has been made flexible by removing some of the wall material.

U.S. Pat. No. 7,879,055 to Stone et al. disclose a suture cutter with an outer member and an actuating inner member. A portion of the outer member is angled and the outer member includes bores or openings.

SUMMARY

In one broad aspect, embodiments of the present invention comprise a suture cutter comprising: a solid outer member defining a lumen there-through; an inner member received at least partially within the lumen, a portion of the inner member defining a curve, the inner member further defining a feature for retaining a strand of suture; and at least one of the inner and outer members being moveable with respect to the other of the inner and outer members for cutting the strand of suture.

In a further broad aspect, embodiments of the present invention comprise a suture cutter comprising: an outer member defining a lumen there-through; an inner member received at least partially within the lumen, the inner member defining a curve, the inner member defining a feature for retaining a strand of suture; the inner member being configured to have an offset-to-diameter ratio of between about 1.1 and about 1.3; and at least one of the inner and outer members being moveable with respect to the other of the inner and outer members to for cutting the strand of suture.

In still a further broad aspect, embodiments of the present invention comprise a suture cutter comprising: an outer member defining a lumen there-through; and an inner member received at least partially within the lumen, a portion of the inner member defining a curve, the inner member further defining a feature for retaining a strand of suture; at least one of the inner and outer members being moveable with respect to the other of the inner and outer members for cutting the strand of suture; and the inner member being deflectable upon movement of the at least one of the inner and outer members with a deflection to baseline value of between about 15% to about 33%.

In another broad aspect, embodiments of the present invention comprise a suture cutter comprising: an outer member defining a lumen there-through; and an inner member at least partially received within the lumen, the inner member defining a curve, the inner member further defining a feature for retaining a strand of suture; at least one of the inner and outer members being moveable with respect to the other of the inner and outer members for cutting the strand of suture; and the outer member being deflectable upon movement of the at least one of the inner and outer members with a deflection to baseline value of less than about 85%.

In still another broad aspect, embodiments of the present invention comprise a suture cutter comprising: an outer member defining a lumen there-through; and an inner member at least partially received within the lumen, the inner member defining a curve, the inner member further defining a feature for retaining a strand of suture, the feature defining a cutting edge that is vertically offset by a distance of between about 0.012" to about 0.026" from a longitudinal axis extending along a top edge of the inner member; at least one of the inner and outer members being moveable with respect to the other of the inner and outer members for cutting the strand of suture; and each of the inner and outer members being deflectable upon movement of the at least one of the inner and outer members, with a cumulative deflection of both the inner and the outer members being approximately equivalent to the offset distance.

In an additional aspect of the invention, embodiments of the present invention comprise a method of cutting suture, the method comprising: loading a suture through a side passage of an inner member of a suture passer and moving at least one of the inner member and an outer member of the suture passer relative to the other of the inner member and the outer member such that an exit from the side passage is obstructed by the outer member, thereby preventing the suture from exiting through the side passage. These embodiments may additional comprise advancing the suture passer along the suture to a desired cutting location, and moving at least one of the inner member and outer member relative to the other of the inner member and outer member to cut the suture at the desired cutting location.

BRIEF DESCRIPTION OF THE DRAWINGS

In order that the invention may be readily understood, embodiments of the invention are illustrated by way of examples in the accompanying drawings, in which:

FIG. 2A is a top, front, left side perspective view of a distal portion of a suture cutter, in accordance with an embodiment of the present invention;

FIG. 2B is a top, rear, right side perspective view of a distal portion of a suture cutter, in accordance with an embodiment of the present invention;

FIG. 2C is a bottom, front, left side perspective view of a distal portion of suture cutter, in accordance with an embodiment of the present invention;

FIG. 6A illustrates a suture cutter comprising multiple passages to provide varying tail lengths, in accordance with an alternative embodiment of the present invention;

FIG. 6B illustrate a cross-sectional of a suture cutter taken along the line 6B-6B of FIG. 6A, in accordance with an embodiment of the present invention;

FIG. 6C illustrates side view of a suture cutter comprising multiple passages terminating in a single cutting edge to provide varying tail lengths, in accordance with an alternate embodiment of the present invention;

Figure 8E:
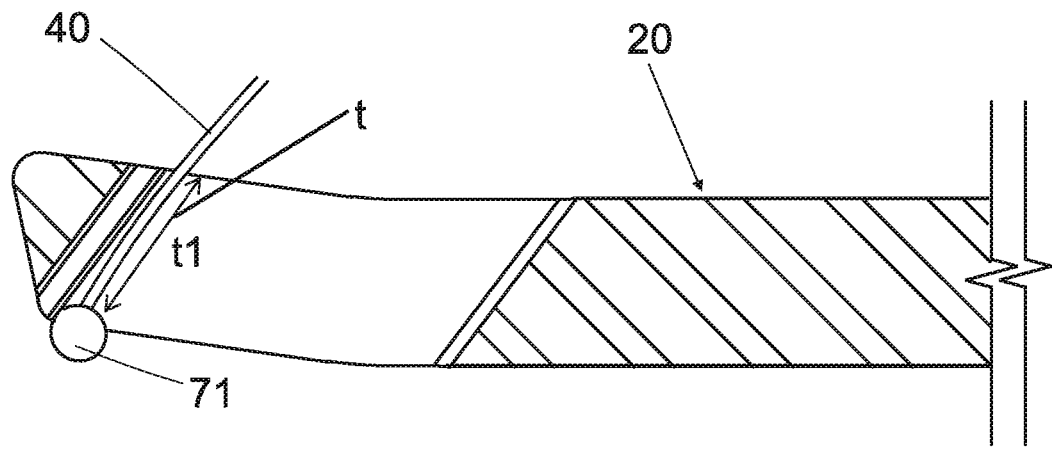
Figure 8F:
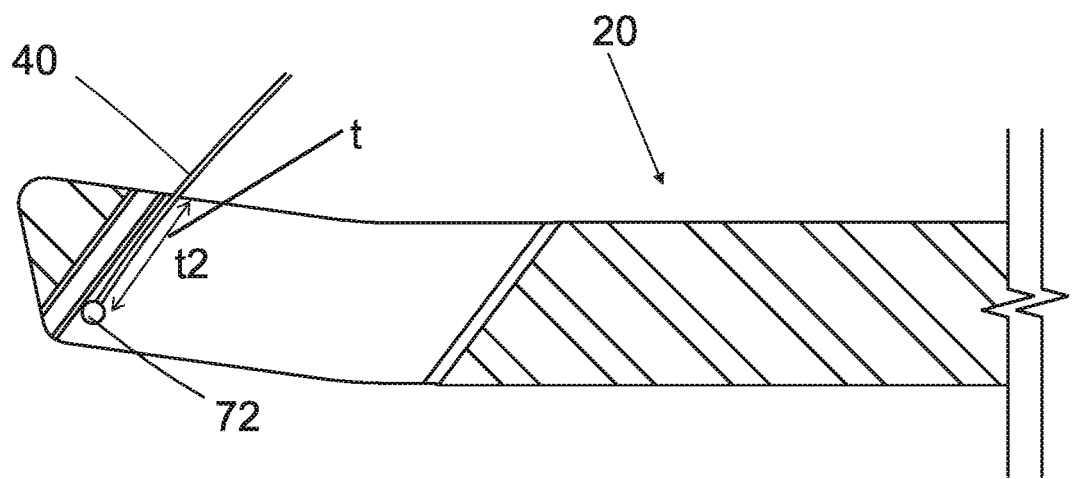
Figure 9A:
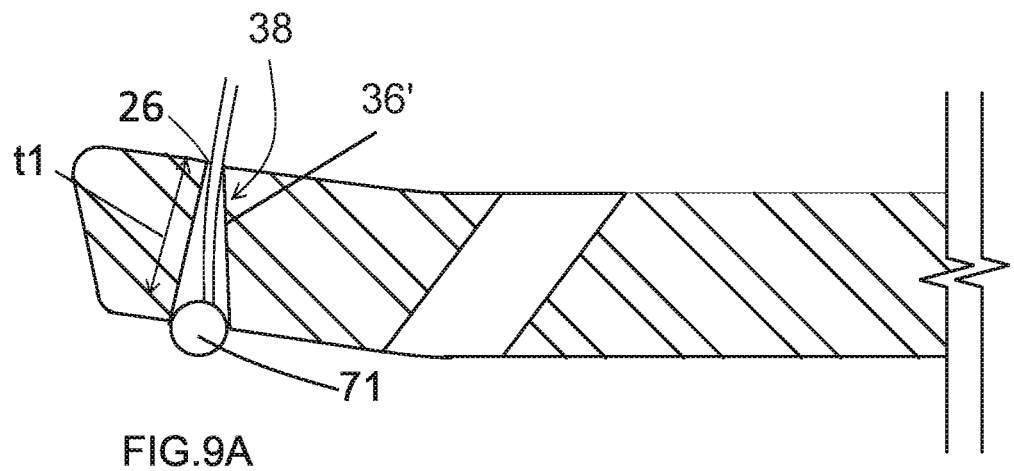
Figure 9B:
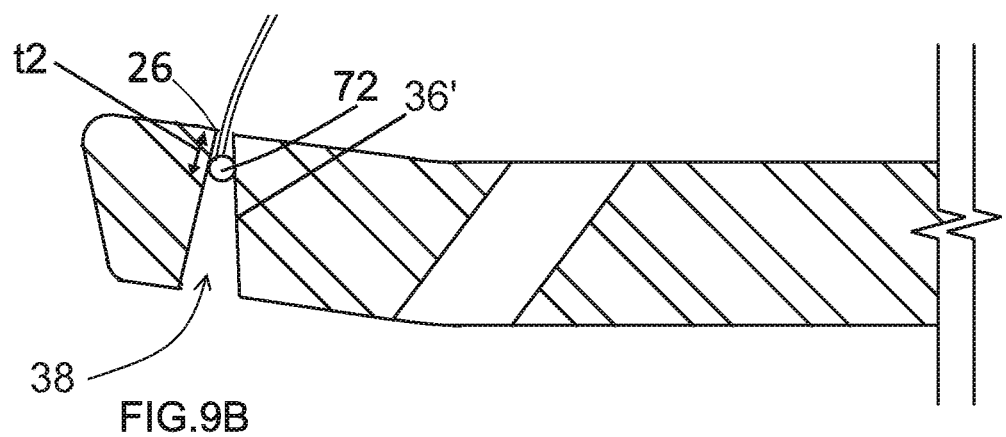
Figure 9C:
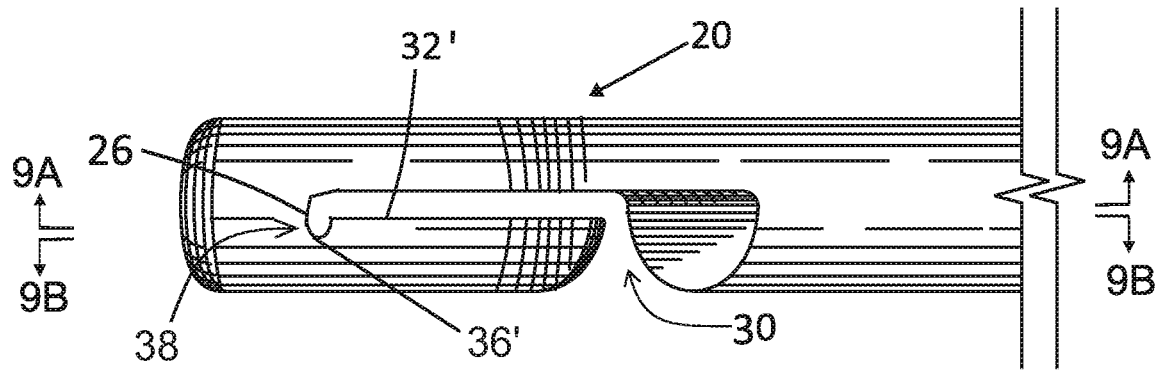
Figure 10A:
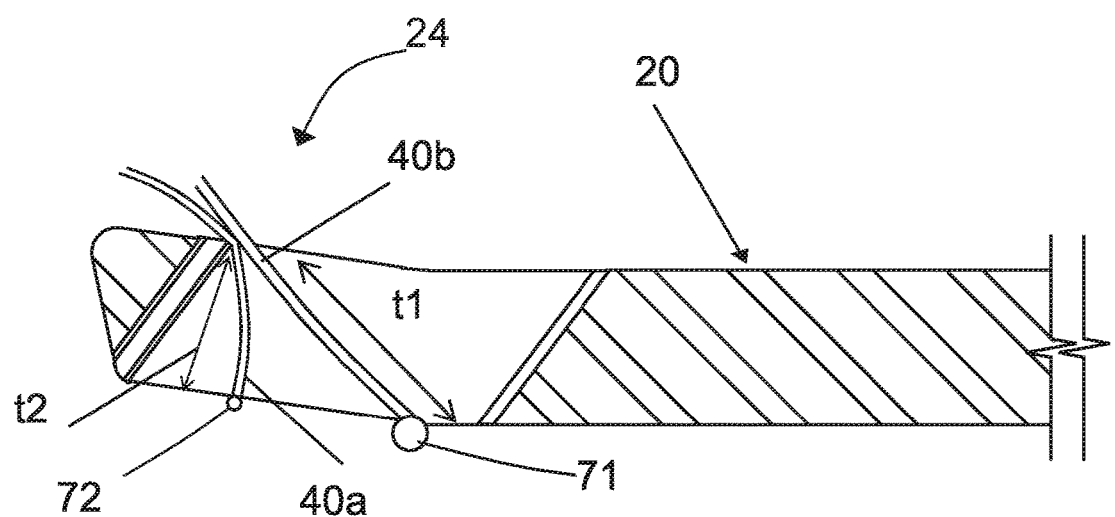
Figure 10B:
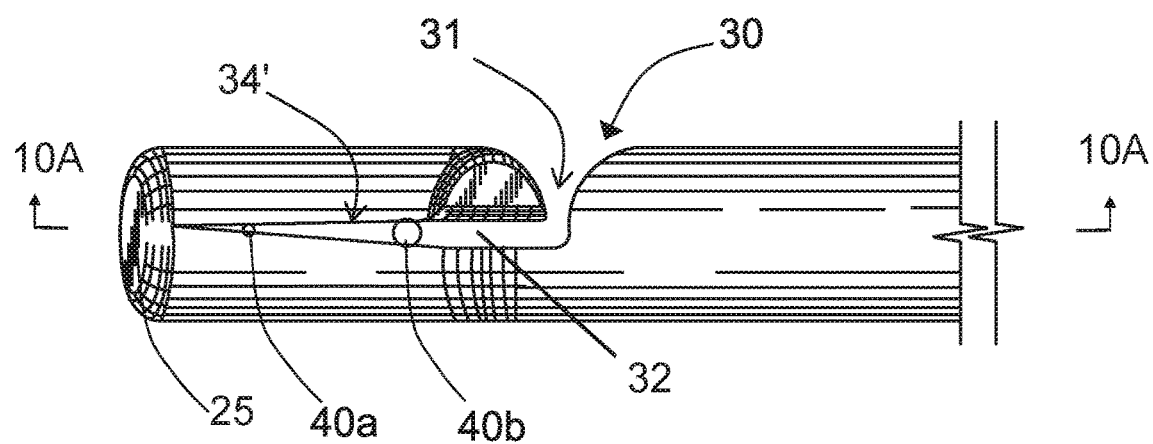
Figure 11:
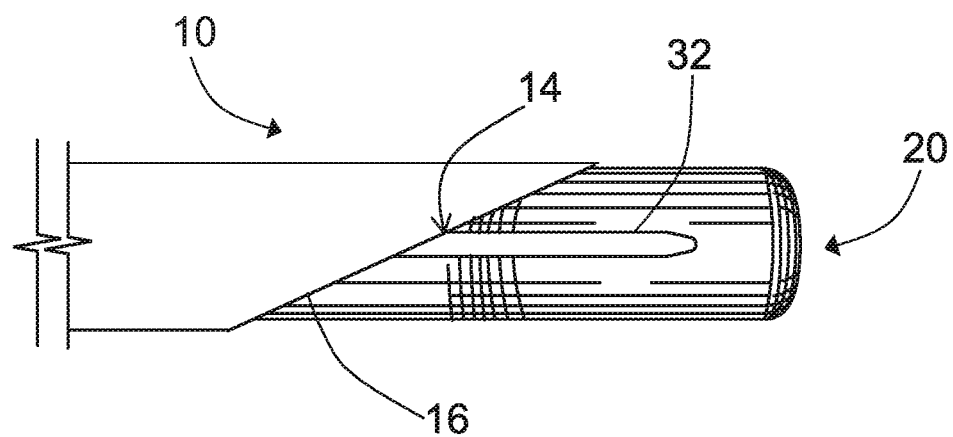
Figure 12A:
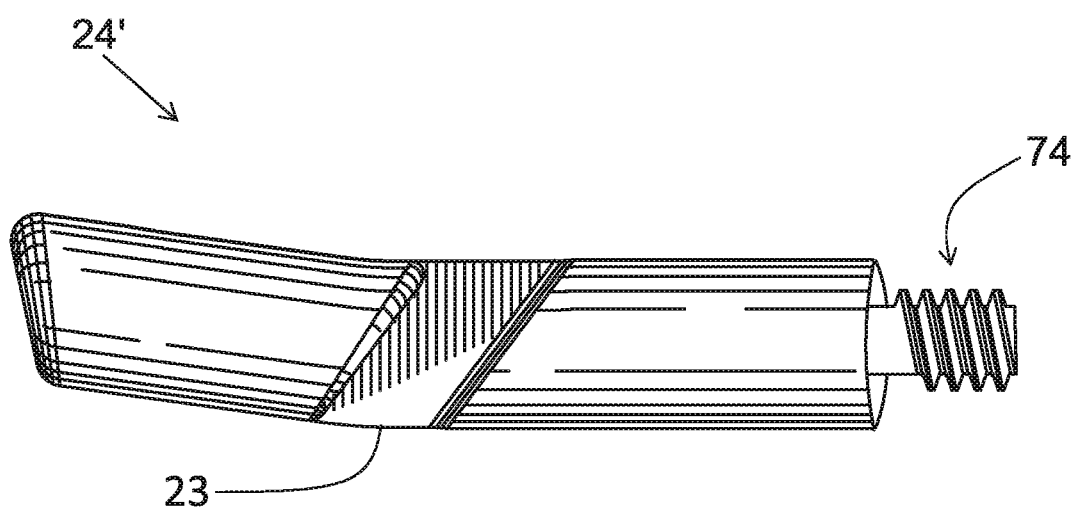
Figures 12B, 12C, 13A:
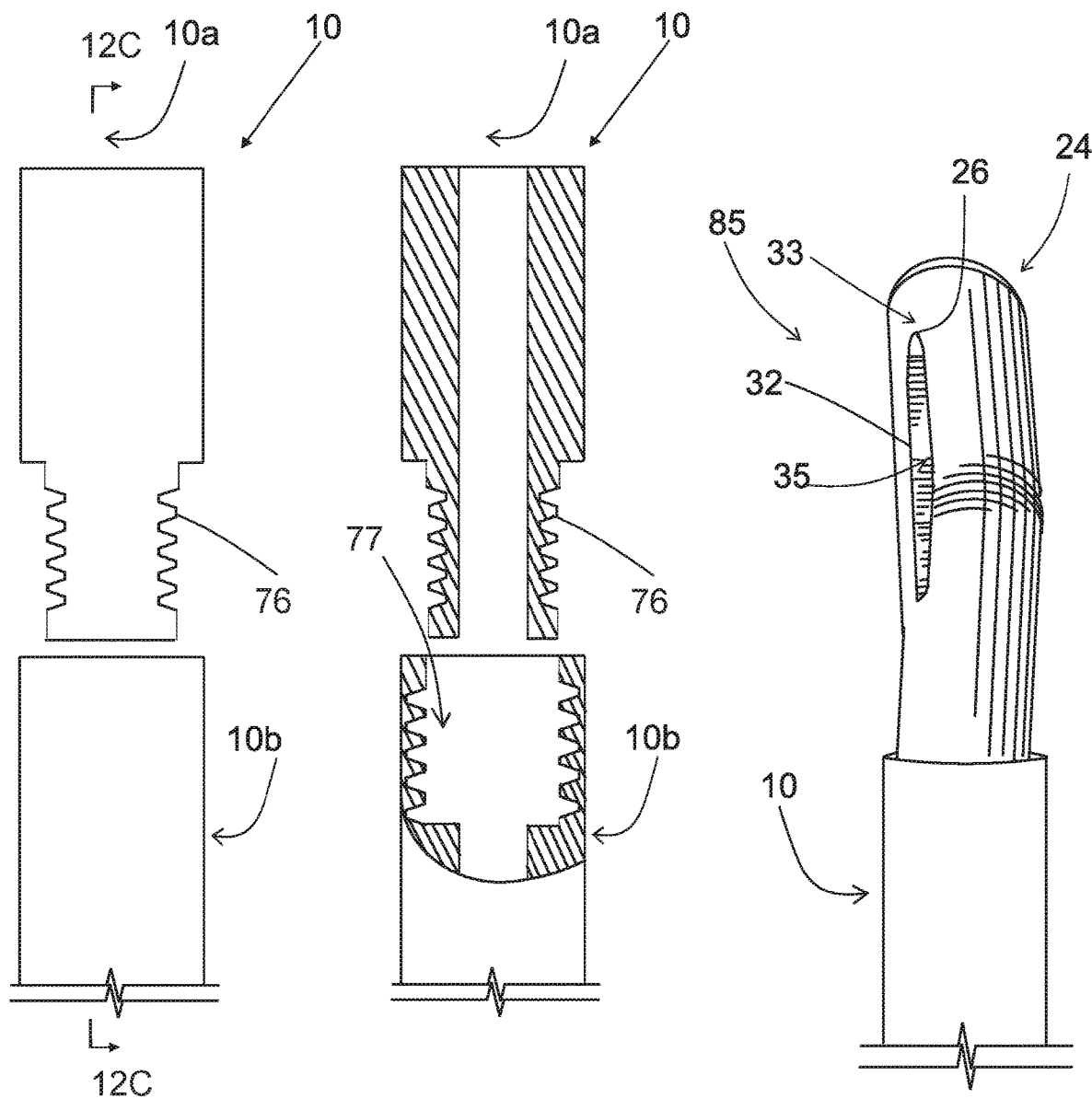
Figure 13B:
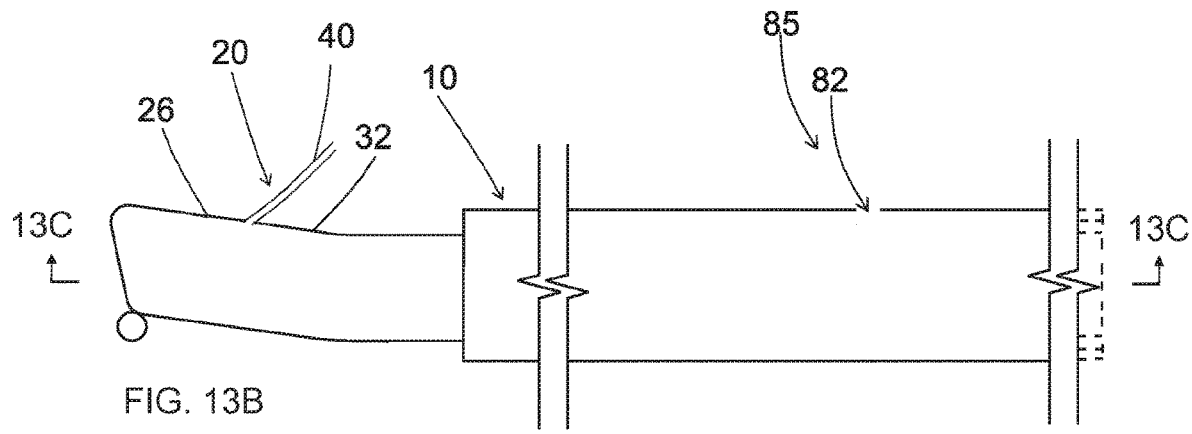
Figure 13C:
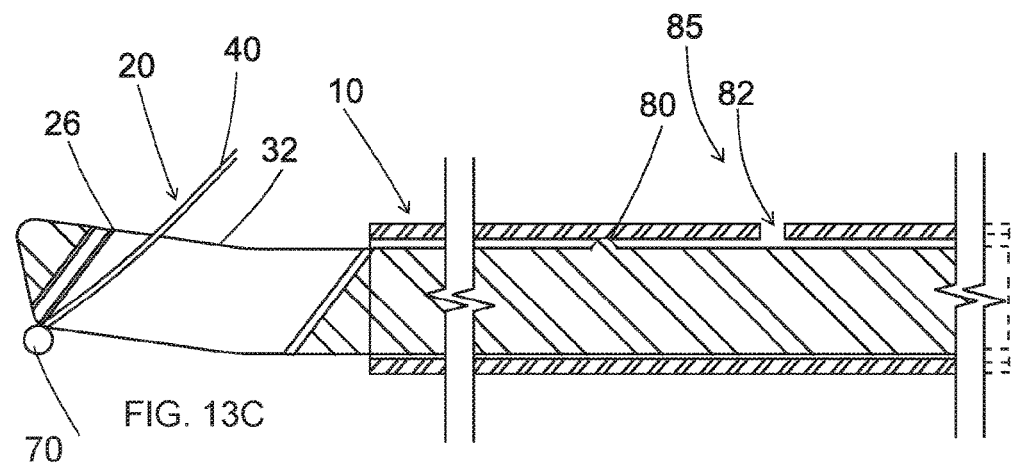
Figure 13D:
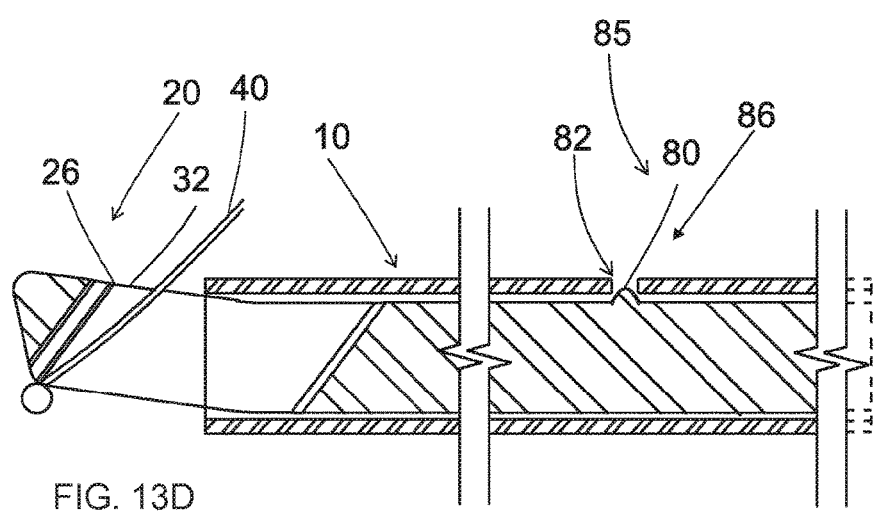
Figure 13E:
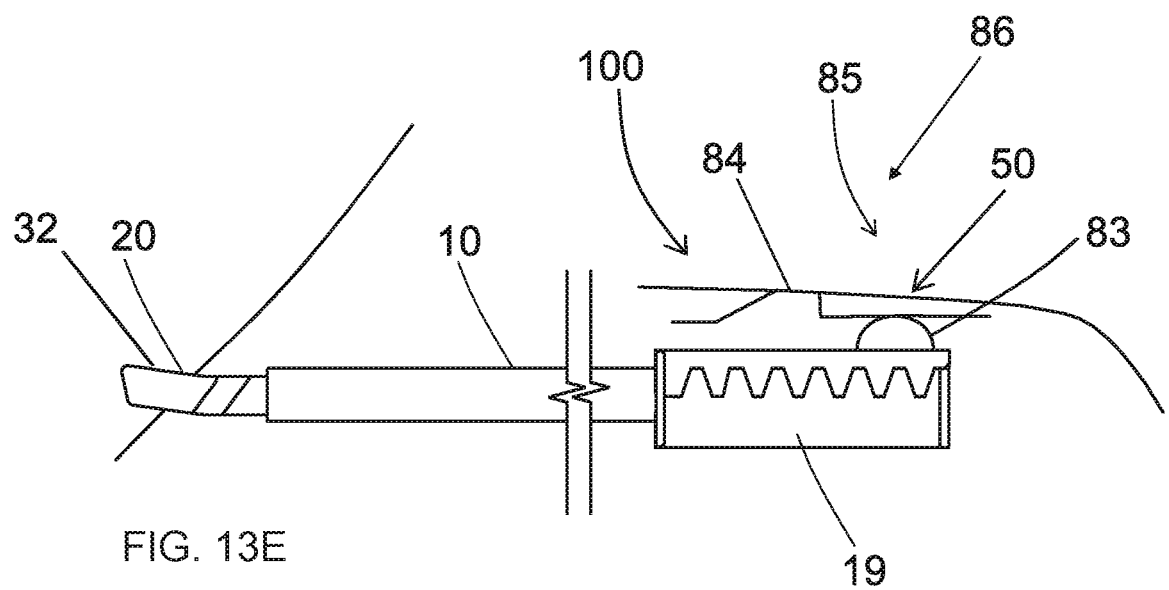
Figure 13F:
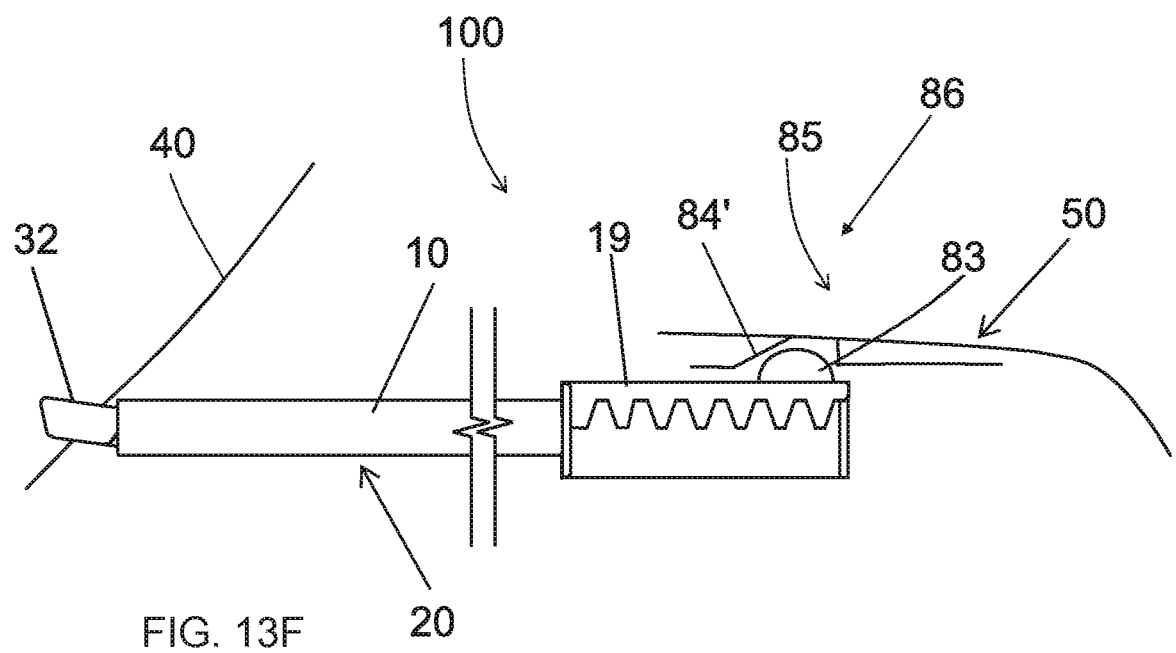
Figure 14:
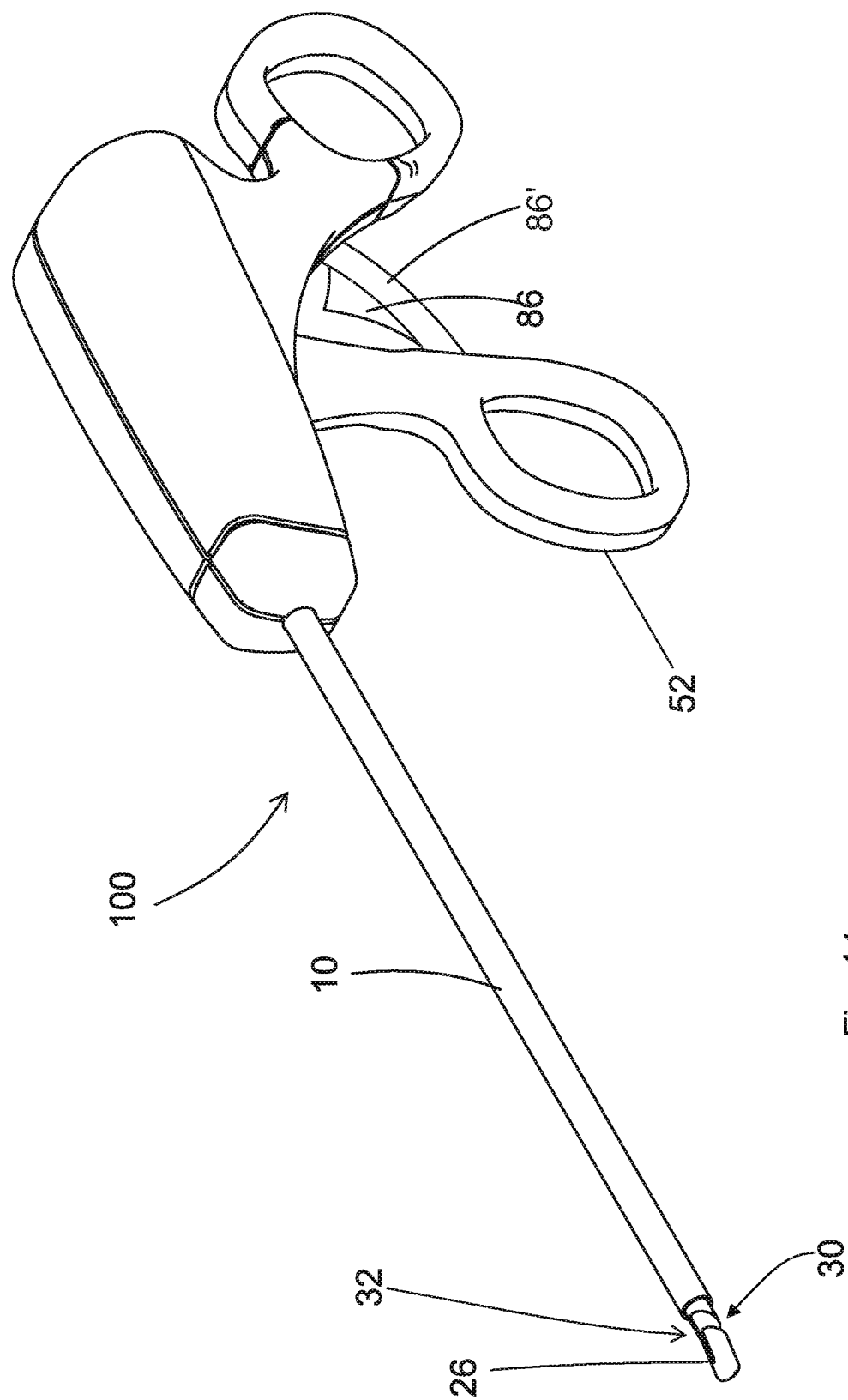

7A-7B illustrate top and perspective views of an inner member of a suture cutter comprising a feature to provide varying tail lengths, in accordance with an alternative embodiment of the present invention;

FIGS. 8A-8D illustrate front views of an inner member of a suture cutter comprising a feature for automatically adjusting the tail length based on suture knot size;

FIG. 8E is a cross-sectional view of the inner member of FIG. 8C taken along the line 8E-8E of FIG. 8C;

FIG. 8F is a cross-sectional view of the inner member of FIG. 8D taken along the line 8F-8F of FIG. 8D;

FIG. 9A is a cross-sectional view of an inner member of FIG. 9C for allowing automatic adjustment of a tail length of a suture in accordance with an alternate embodiment of the present invention, the cross-sectional view taken along the line 9A-9A of FIG. 9C;

FIG. 9B is a cross-sectional view of an inner member of FIG. 9C, taken along the line 9A-9A of FIG. 9C, in accordance with an alternate embodiment of the present invention;

FIG. 9C is a side view of an inner member for a suture cutter for allowing automatic adjustment of a tail length of a suture in accordance with an alternate embodiment of the present invention;

FIG. 10A is cross-sectional view of an inner member of FIG. 10B for allowing automatic adjustment of a tail length of suture based on suture size, in accordance with an alternate embodiment of the present invention, the cross-sectional view being taken along the line 10A-10A of FIG. 10B;

FIG. 11 is side view of a distal portion of a suture cutter with an outer member comprising a bevel edge in accordance with an alternate embodiment of the present invention;

FIG. 12A is a side view of a removable distal tip of the inner member in accordance with an embodiment of the present invention;

FIG. 12B is a side view of an outer member comprising a removable distal end, in accordance with an embodiment of the present invention;

FIG. 12C is a cross-sectional view of FIG. 12B taken along the lines 12C-12C of FIG. 12B, in accordance with an embodiment of the present invention;

FIG. 13A is a perspective view of distal portion of an inner member comprising an enclosed slot, in accordance with an embodiment of the present invention;

FIG. 13B illustrates a side view of a suture cutter comprising a locking feature in accordance with an alternative embodiment of the present invention;

FIG. 13C is a cross-sectional view of FIG. 13B taken along the line 13C-13C of FIG. 13B, in accordance with an embodiment of the present invention;

FIG. 13D is a cross-sectional view illustrating the suture cutter of FIGS. 13B and 13C in a partially actuated position in a locked configuration accordance with an embodiment of the present invention;

FIGS. 13E-13F illustrate a suture cutter with a locking feature, in accordance with an alternative embodiment of the present invention; and FIG. 14 illustrates a suture cutter with a locking feature comprising a locking ramp in a still further alternative of the present invention.

DETAILED DESCRIPTION

In some surgical procedures that involve the use of sutures, including procedures that may be performed within a patient's body, a suture cutter may be required in order to cut free ends of a suture or excess suture. For example a suture cutter may be required to cut excess suture exiting a knot in an inaccessible or difficult to reach area within a patient's body.

Various suture cutters available in the field include an inner member and an outer member. Some such suture cutters provide members that do not necessarily substantially interact with one another in order to cut the suture. In some such examples, where there is limited interaction between the inner and outer members, the members may not be able to generate sufficiently high forces in order to cut high strength sutures or multiple sutures including multifilament sutures.

In other suture cutters utilizing inner and outer members, the members interact with one another in order to cut the suture. Typically, in such cases, one of the inner and outer members is moveable relative to the other to cut the suture. However, such suture cutters are generally somewhat flexible by providing apertures, slots or cut-outs within the outer member or additionally by providing an inner member made of a flexible material. Such suture cutters therefore typically rely on an outer member which is not substantially solid. Due to this flexibility in the outer (and possibly inner) member, these suture cutters limit the amount of force that is applied to the suture, and as such also do not provide sufficient force to cut high strength sutures or multiple sutures such as multi-filament sutures.

Therefore, unlike the devices known in the art, the present inventors have designed and reduced to practice a novel suture cutter that comprises a two-member assembly that utilizes interaction between the inner and outer members in order to generate sufficiently high forces consistently to cut high strength and/or multiple sutures including multi-filament sutures. The present inventors have discovered that, in order to generate these required forces, the spring constant or k-value of the suture cutter assembly should be maximized. In such a dual-member system, the k-value is dominated by the weaker or softer member. Thus, the present inventors have discovered and reduced to practice a suture cutter assembly that provides a solid outer member, i.e. an outer member that substantially lacks an aperture, slot, window or cut-out in a side-wall thereof, that aims to maximize the k-value of the assembly, for example by helping maximize the k-value of the weaker member, and thereby provides a consistent k-value for the system and thus a consistent shearing force. In addition, embodiments of the present invention include a suture cutter having a limited or constrained outer diameter as there may be limited room to manoeuvre when accessing the target area within the patient's body.

More specifically, the present inventors have developed a suture cutter assembly that provides a solid outer member and a curved inner member for maximizing the k-value of the assembly and ensuring consistent application of shearing forces on the suture(s). The curved inner member additionally provides a side slot to allow the inner member to accommodate varying number of sutures including high strength and/or multiple or multi-filament sutures. The curved inner member and the solid outer member interact with one another to generate forces sufficient to cut high strength suture and/or multiple sutures, including multi-filament sutures, while maintaining a limited or constrained OD of the suture cutter assembly.

In some embodiments, the suture cutter assembly of the present invention additionally provides limited flexion between the inner and outer members as the shearing force is generated in order to increase the efficacy of cutting. Thus, the suture cutter of the present invention may be used to cut monofilament/single stranded sutures or high strength or flexible stranded/multifilament sutures such as UHPE (e.g. Ultra-high-molecular-weight polyethylene) multi-filament sutures that require a higher shear force to cut the suture as the cumulative OD (outer diameter) of the suture strand increases with the number of filaments.

In some embodiments, the inner member may additionally comprise a maximized OD to accommodate the multi-filament and/or multiple sutures. Additionally, in some embodiments, the maximized OD of the inner member may additionally help maximize the tail length of cut suture, for example in procedures where the suture cutter is used to cut or trim free ends of a suture forming a knot.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Suture Cutter Device

Figure 1A:
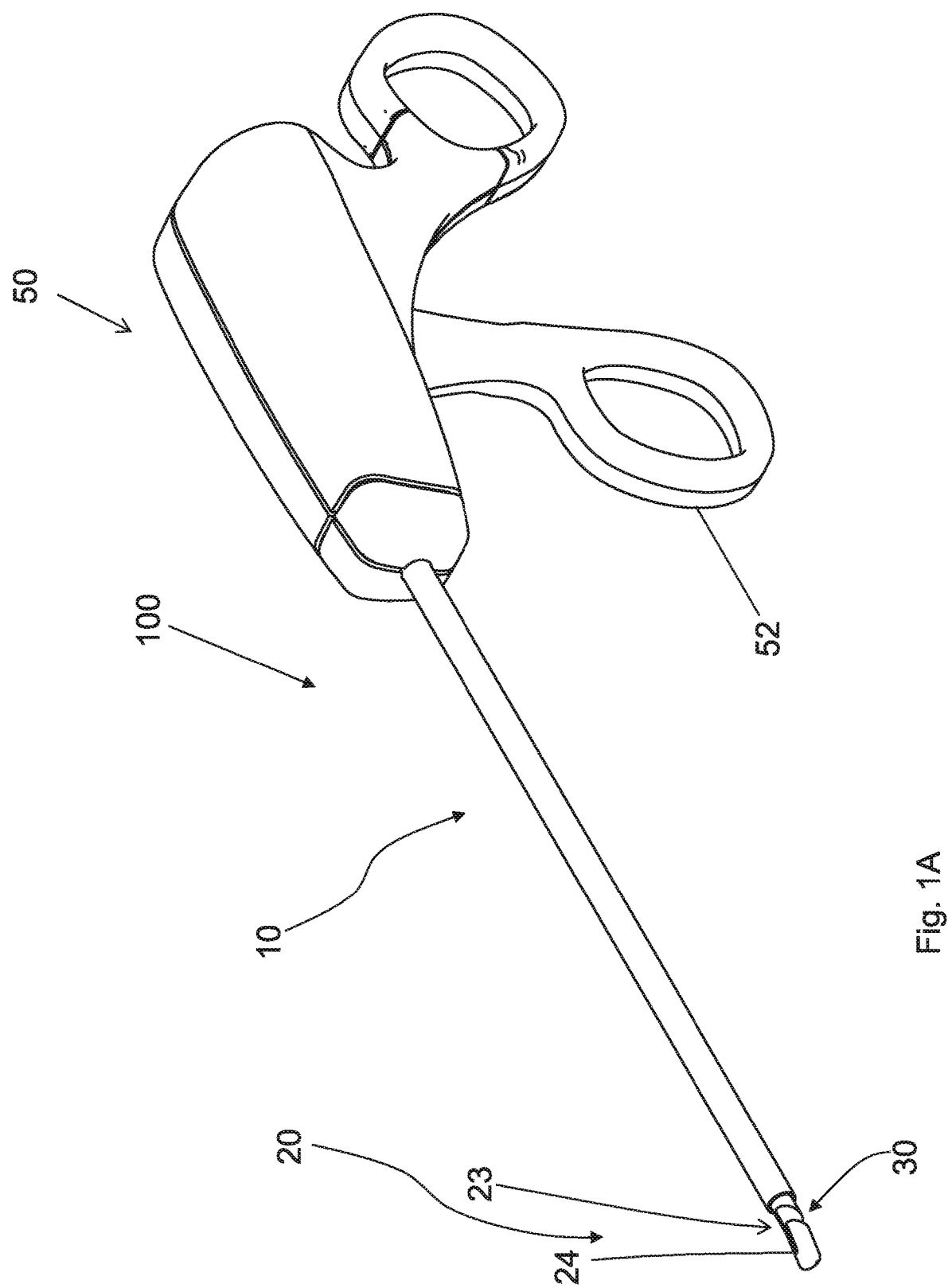
FIG. 1A is a perspective view of a suture cutter in accordance with an embodiment of the present invention.
Figure 1B:
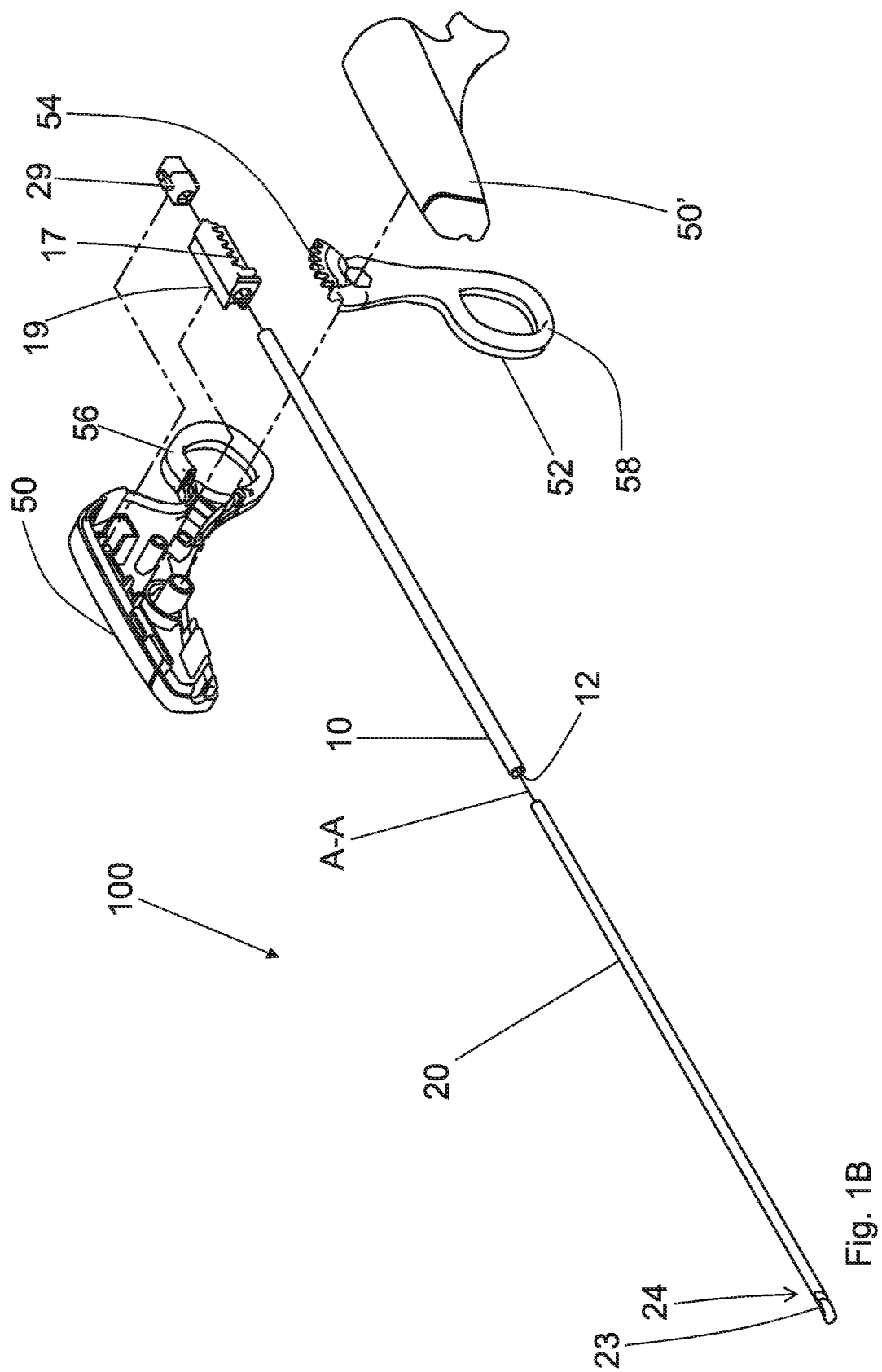
FIG. 1B is an exploded view of a suture cutter in accordance with an embodiment of the present invention.

In accordance with an embodiment of the present invention, as shown in FIGS. 1A and 1B, a device 100 is provided for cutting suture. The device or suture cutter 100 comprises an outer member or cannula 10 and an inner member or elongated shaft 20. The outer member 10 extends longitudinally along a device longitudinal axis A-A [FIG. 1D] and defines a lumen 12 for receiving the inner member 20. The inner member 20 is received within the outer member 10 such that the proximal portion of the inner member 20 is coaxial with the outer member 10 and extends along the device longitudinal axis, whereas a distal portion or tip 24 of the inner member 20 defines a curve or bend 23. The inner member 20 is coaxially offset from the outer member 10 along the curve 23. The outer member 10 and the curved inner member 20 are moveable reciprocally with respect to one another in order to cut a suture that is held along the curve 23 of the inner member 20. In one embodiment, the outer member 10 is moveable distally in a longitudinal direction with respect to the inner member 20. Alternatively the inner member 20 may be moveable proximally with respect to the outer member 10. In some such examples, the position of the inner member 20 may be rotationally independent from the outer member 10. In other words, regardless of the rotational orientation of the inner member 20, the inner member 20 is functional to cut suture when for example the outer member 10 is advanced distally. In the particular example shown, the inner member 20 defines an opening 30 for receiving and retaining a suture within the distal tip 24, and outer member 10 is moveable over the inner member 20 upon actuation of a trigger 52 in order to cut the suture.

In some embodiments, the outer member 10 comprises a solid cylindrical or tubular member defining the lumen 12 there-through and the rigidity of the outer member 10 has not been compromised through the introduction of openings or slots along its length. In a particular example, the outer member 10 comprises a 304 stainless steel. With reference now to FIG. 1C, in some such embodiments, the outer member 10 has an outer diameter (OD) that ranges from between about 0.160" to about 0.170" and an inner diameter (ID) that ranges from between about 0.132" to about 0.138". In some embodiments, with reference to FIG. 1C, the wall thickness T of the outer member 10 is between about 0.013" to about 0.017". In a specific example, the outer member 10 has an OD of about 0.165" and an ID of about 0.135" with a wall thickness equal to about 0.015".

In some embodiments the inner member 20 comprises a solid shaft along a proximal portion that defines a solid interior. Similar to the outer member 10, in some embodiments the inner member 20 is also made from stainless steel and may comprise a 440 stainless steel. In a specific example, the inner member 20 comprises a 440C stainless steel and has an outer diameter that ranges from between about 0.120" to about 0.130". In one specific example, the inner member has an outer diameter (OD) equal to about 0.125". Alternatively in some examples, the inner member 20 may define a hollow interior.

Figure 1D:
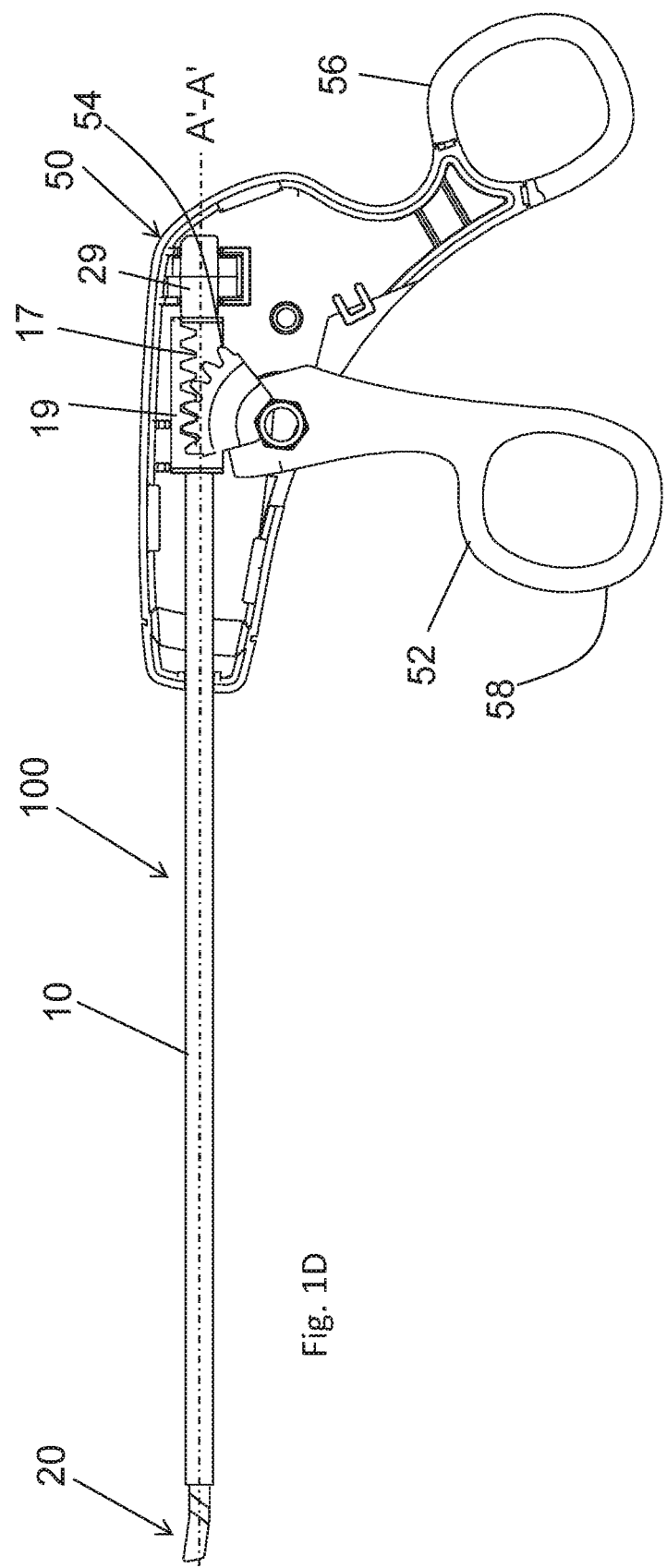
FIG. 1D is a partial cut-away view of a suture cutter in accordance with an embodiment of the present invention.
Figure 1C:
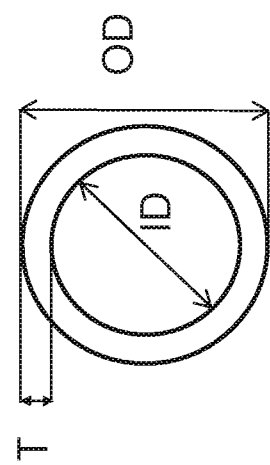
FIG. 1C is a cross-sectional view of an outer member of the suture cutter, in accordance with an embodiment of the present invention.

As shown in FIGS. 1B and 1D, the device 100 further comprises a handle housing 50. A cannula hub 19 is held within the handle housing 50 and is coupled to the outer member or cannula 10 to form an integral unit therewith. The handle housing 50 also contains a shaft hub 29 that is coupled to the shaft of the inner member 20. In some embodiments, for assembly, a portion of the inner member 20 may be initially received through the outer member 10, the cannula hub 19 and into the shaft hub 29 to be coupled thereto. The handle housing terminates in a grip 56 to allow the user to manipulate the device 100. The device 100 further comprises a trigger 52 where a portion of the trigger 52 is also held within the handle housing 50. The handle housing 50 additionally comprises a cover 50' for securing the hubs 19, 29, the inner and outer members 20, 10 and the trigger 52 within the handle housing 50. In some embodiments, the trigger 52 forms the actuation mechanism for advancing the outer member 10 over the inner member 20. The trigger 52 co-operatively engages with the cannula hub 19 and functions to distally advance the outer member 10 as the trigger is pulled. In a particular embodiment as shown, the trigger 52 has a grip 58 at one end and teeth 54 at an opposing end that engage with teeth 17 of the cannula hub 19, allowing the trigger 52 to translate the cannula hub 19 to allow advancement of the outer member 10 over the inner member 20. Alternatively, the trigger 52 may co-operatively engage with the shaft hub and may function to cause proximal movement of the inner member 20 relative to the outer member 10. Still furthermore, the trigger mechanism may function to cause movement of the outer member 10 and the inner member 20 relative to one another in order to cut the suture.

With reference now to FIGS. 2A-2C, the distal end or tip 24 of the inner member 20 is shown having a curve or bend 23. As mentioned previously and as shown in FIG. 2A, the curved distal tip 24 defines an opening 30 for receiving and retaining a suture. The opening 30 defines a passage 31 through which the suture is inserted and comprises a slit/window/side slot or slot 32 that functions as a retaining feature for retaining the suture within the opening 30. In some embodiments as shown the slot 32 is a side loading slot. In some embodiments, the passage or slot 32 may be usable by either a right-handed user or a left-handed user, in order to load the suture. In some such embodiments, the solid outer member 10 is symmetric about the longitudinal axis A-A as shown in FIG. 1C and as such may permit adjustment of the rotational orientation of the inner member 20. For example, the rotational orientation of the inner member 20 may be adjusted during manufacturing or prior to use to orient the slot 32 for a right-handed configuration or a left-handed configuration.

As shown in FIG. 2C, the slot 32 extends perpendicularly to a second longitudinal axis A'-A' along the curved distal tip 24, and extends from the top edge of the distal tip 24 through to the bottom edge of the distal tip 24. With reference now to FIG. 2B, the slot 32 terminates in a distal cutting edge 26 and the cutting edge 26 also functions as a retaining feature for retaining the suture. The region of the distal tip 24 that is distal to cutting edge 26 forms the distal edge portion 28. In one specific example, the distal edge portion 28 has a longitudinal length of about 0.082" to about 0.084".

Figure 2F:
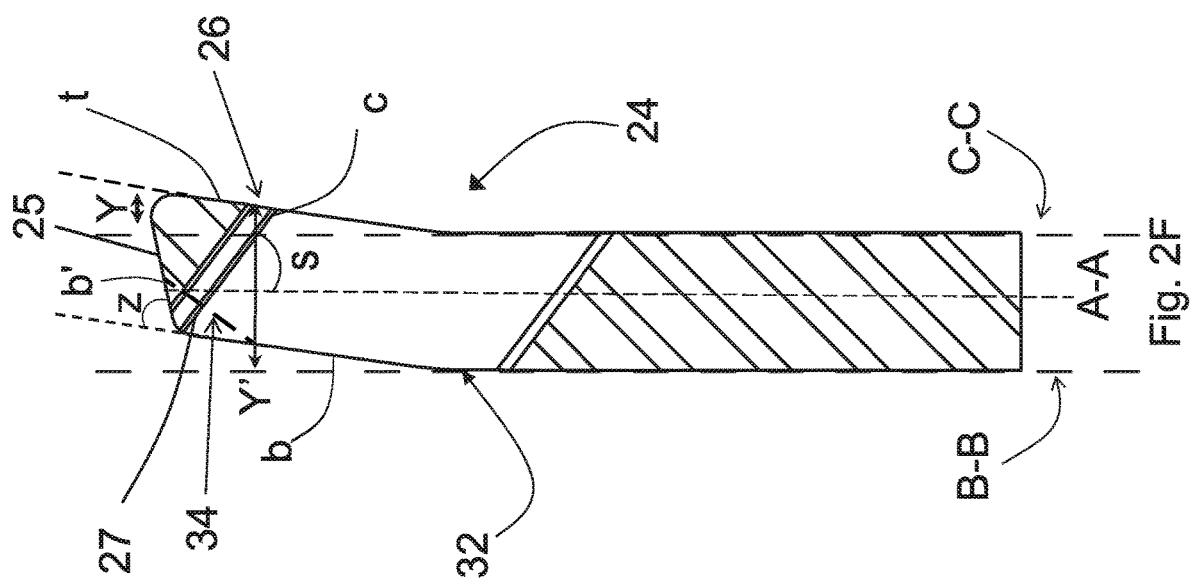
FIG. 2F is a cross-sectional view of the distal portion of the suture cutter, taken along the line 2F-2F of FIG. 2D.
Figure 2E:
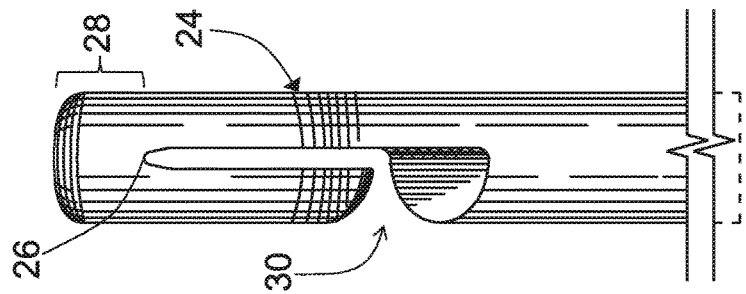
FIG. 2E is a bottom plan view of a distal portion of the suture cutter, in accordance with an embodiment of the present invention.
Figure 2D:
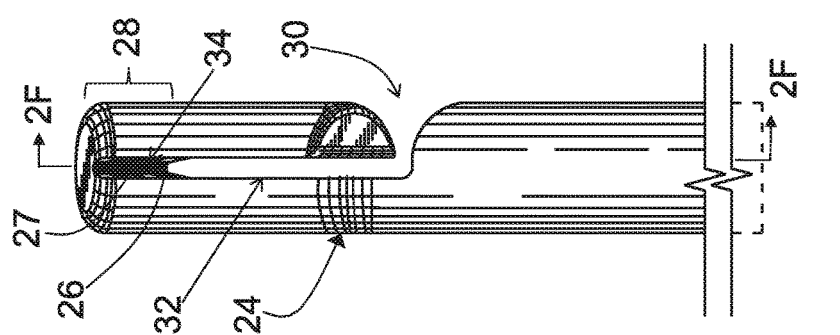
FIG. 2D is a top plan view of a distal portion of the suture cutter, in accordance with an embodiment of the present invention.
Figure 2G:
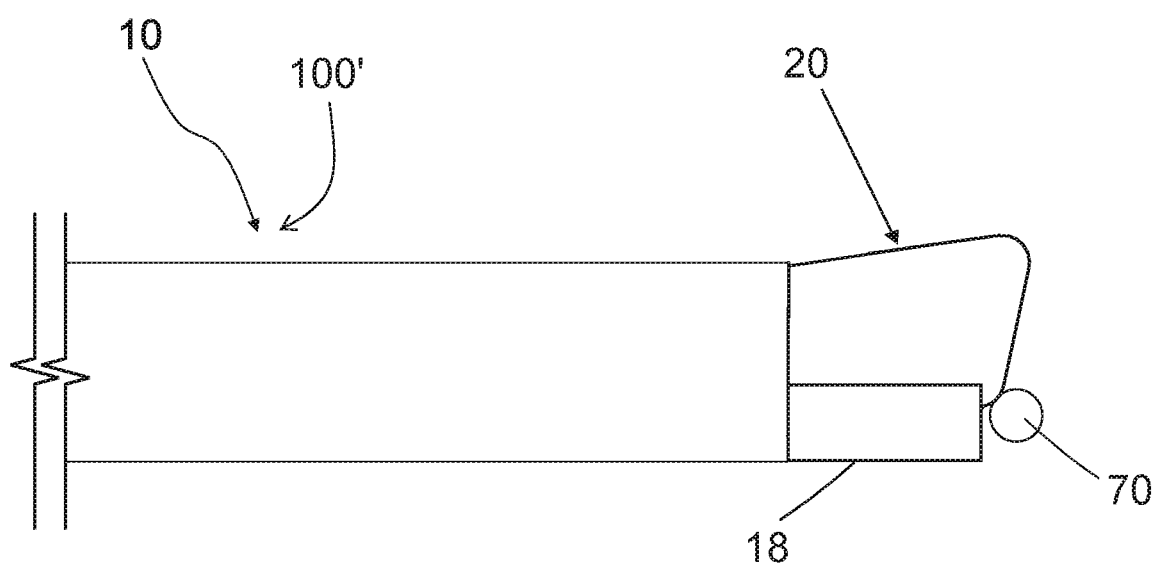
FIG. 2G is a side view of a distal portion of a suture cutter comprising a guiding flange in accordance with an alternate embodiment of the present invention.

As shown in FIGS. 2D and 2E, the distal edge portion 28 has an under-cut or interior edge 27 that forms a groove 34 that is in communication with the slot 32 and extends along the distal edge portion 28. In other words a bottom portion of the slot 32 terminates at the distal groove 34 at the distal surface of the distal tip 24. Material is cut or removed from under the distal edge portion 28 to form the distal cutting edge 26 that can exert sufficient pressure against the suture to cut the suture during actuation of the outer member 10. The groove 34 in conjunction with a bottom portion of the slot 32 functions to hold a knot in place to allow the suture strands exiting the knot to be placed along the under-cut or inside edge 27 to allow the suture strands to be cut at the cutting edge 26. As such the under-cut or inside edge 27 defines an inside edge length, where the inside edge length is substantially equal to the length of the cut suture or in other words the tail length of the suture. Alternatively, in some embodiments, as shown in FIG. 2G, a suture cutter 100' is provided having an outer member 10 comprises a guiding flange 18 along a distal end of the outer member 10 for example along a bottom portion thereof to push the knot 70 as shown in order to ensure that the knot is positioned within the groove 34 against the distal face in order to ensure that the tail length is defined by the cut-out or inside edge 27. Alternatively, in some embodiments the tail length may be defined by an outer diameter of the inner member 20. For example in some embodiments the knot may rest against a bottom portion of the slot 32 away from the distal surface of the distal tip 24 which may provide a tail length that is equal to the outer diameter of the inner member 20 and more specifically it is equal to the distance between the knot (as it rests against the bottom portion of the slot 32 away from the distal surface) and the cutting edge 26.

In some embodiments, the distal cutting edge 26 may be blunt. In some embodiments, the cutting edge 26 may additionally comprise a sharp edge which may allow cutting of the suture in addition to shearing it. More specifically, with reference now to FIG. 2F, which shows a side cross-sectional view of the distal tip 24, the under-cut 27 is defined at an angle with respect to the device longitudinal axis A-A. In one example, the angle s of the under-cut 27 ranges from about 50 degrees to about 56 degrees from the device longitudinal axis A-A. In some embodiments where the suture cutter of the present invention is used to cut suture tails of a knot, the distance between the bottom of the slot 32 to the top of the slot 32 along the under-cut 27 defines the cut length of the suture tails or the tail length.

With reference again to FIG. 2F, the cutting edge 26 is at a vertical offset Y' measured from the axis/plane B-B (which is parallel to the device longitudinal axis A-A but extends along the base or bottom of the inner member 20 along its proximal portion, as shown). In other words the vertical offset Y' is measured from an opposing edge of the inner member 20 (that is the edge of the inner member is along the opposing side of the inner member 20 from the cutting edge 26). In some embodiments, the vertical offset Y' has a value that is less than about 0.146", for example between about 0.142" to about 0.146" (3.61 mm to about 3.71 mm). In one specific example, the cutting edge 26 is at a vertical offset Y' that is equal to about 0.144". In this specific example, an offset-to-diameter ratio which is the ratio of the vertical offset Y' to the outer diameter, is equal to about 0.144/0.125 which is less than about 1.2, and is approximately equal to about 1.15. In other embodiments depending on the outer diameter and the vertical offset Y', the offset ratio may be between about 1.1 and about 1.3. In other embodiments having different dimensions, the vertical offset Y' will have values outside of this range, for example greater than 0.146". The offset of the cutting edge 26 may prevent the device 100 from binding as the trigger 52 is actuated to advance the outer member 10 over the inner member 20 to cut the suture. Additionally, in some embodiments, the inner member 20 comprises a tapered distal end face 25, which may be tapered at an angle z that is between about 68 degrees to about 74 degrees from the lower or bottom edge of the distal tip 24. In a specific example, as shown in FIG. 2F, the distal end face 25 is at an angle z that is equal to about 71 degrees. Angle z of the tapered distal end face 25 may help the inner member 20 push against a knot in order to allow the free ends of the suture exiting the knot to be cut using the suture cutter 100.

Figure 3C:
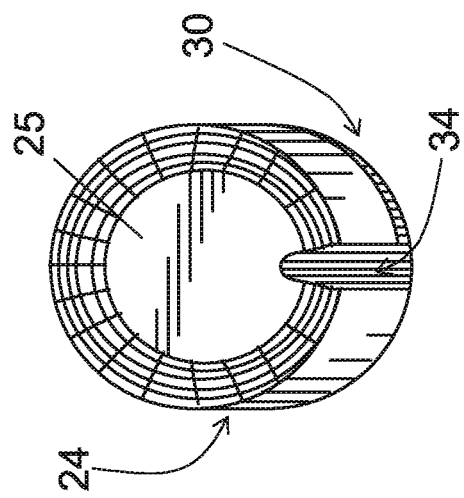
FIG. 3C is a front elevational view of a distal portion of the suture cutter, in accordance with an embodiment of the present invention.
Figure 3D:
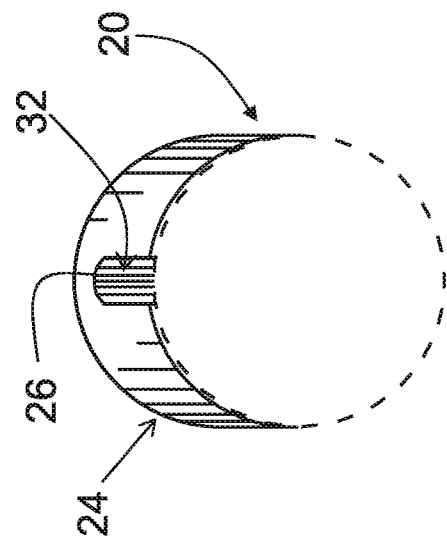
FIG. 3D is a rear elevational view of a distal portion of the suture cutter, in accordance with an embodiment of the present invention.
Figure 3B:
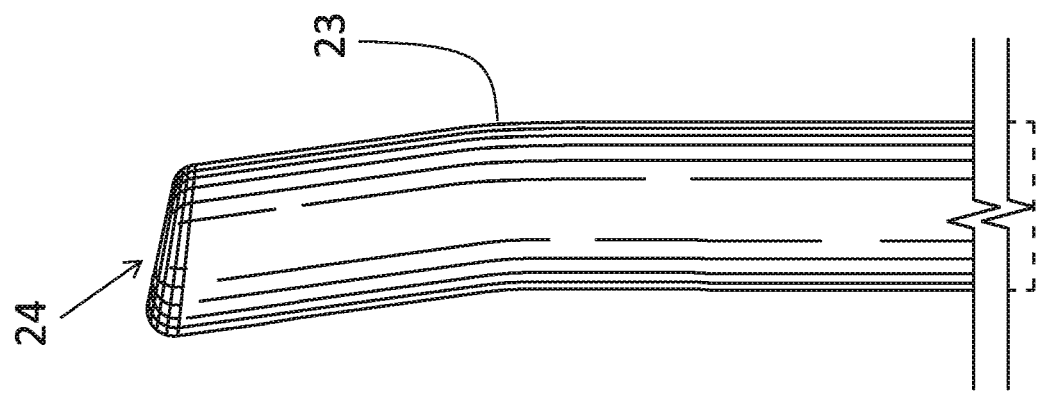
FIG. 3B is a right side elevational view of a distal portion of the suture cutter, in accordance with an embodiment of the present invention.
Figure 3A:
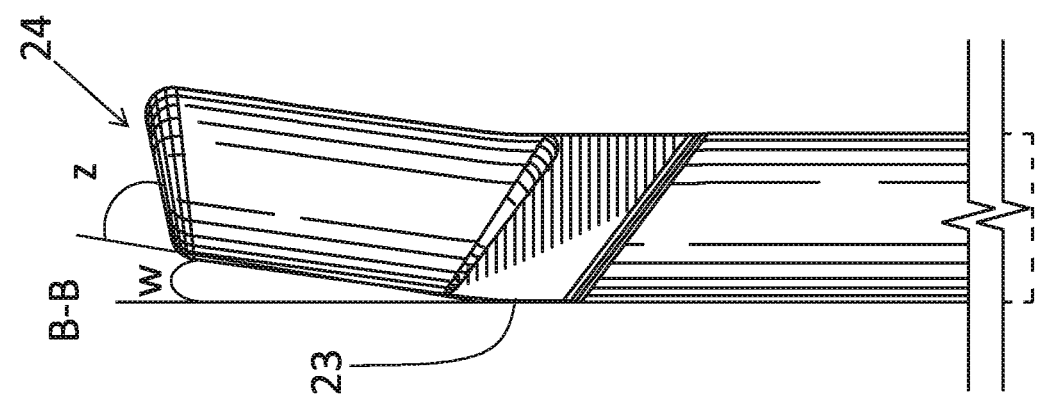
FIG. 3A is a left side elevational view of a distal portion of the suture cutter, in accordance with an embodiment of the present invention.

The distal tip 24 is illustrated further with reference now to FIGS. 3A and 3B. The distal tip 24 has a bend 23, as discussed previously herein above. In some embodiments, the bend 23 may be at an angle w (or in other words has a curvature) that ranges from between about 6 degrees to about 8 degrees. In other words the shaft tip angle w of the distal tip 24 is equal to about 6 degrees to about degrees. Angle w is defined with reference to the device longitudinal axis A-A (or axis B-B, as shown). In a specific example, the curve or bend 23 has an angle w that is equal to about 7 degrees. In some embodiments, the portion of the distal tip 24 along the bend 23 is coaxially offset from the device longitudinal axis, as illustrated further in FIGS. 3C and 3D (where the distal tip 24 is shown and the remaining device shown as extending out of the page or into the page, respectively). The bend 23 may help to position/create the cutting edge 26 at its vertically offset location. Furthermore, in some embodiments, the angle w of the bend 23 helps create interference between the outer member 10 and the inner member 20, as the outer member 10 is advanced over the inner member 10 to cut the suture, and may additionally help prevent the device 100 from binding by allowing the inner member 20 to bend as the outer member 10 is advanced over it in order to cut the suture. Furthermore, in some embodiments of the present invention, the outer member 10 may be provided with a smooth inner surface in order to reduce wear on the cutting edge 26 of the inner member 20. In this instance the outer member 10 or the leading edge is hardened. Alternatively, the inner member 20 may be hardened. In some such embodiments of the present invention, the inner member 20 may be provided with a smooth outer surface in order to reduce wear on the leading edge 14 of the outer member 10.

In some embodiments, as outlined previously a device 100 is provided for cutting suture that defines a system comprising a curved inner member 20 and a solid outer member 10, with the system being usable to create a shearing force through interference between the inner and outer members 20, 10. The shearing force is primarily defined as F=kx where k is the k-value or spring constant of the system and x is the position of the cutting edge 26 on the inner member 20. (More specifically, x is defined as the vertical offset Y of the cutting edge 26 with respect to the axis C-C of the inner member 20 as shown in FIG. 2F and as described previously herein). In some embodiments, the vertical offset Y=vertical offset Y'−Outer Diameter of the inner member 20. The vertical offset Y defines the vertical displacement of the inner and/or the outer members 20, 10 upon actuation. In some embodiments, the combined vertical displacement of the inner and outer members 20, 10 is substantially equal to the vertical offset Y. Thus, in order to adjust the shearing force, either the k-value of the system may be adjusted or the vertical offset Y of the cutting edge may be altered.

Thus, in some embodiments, the shearing force may be adjusted by changing the position x of the cutting edge 26 (or in other words, the offset Y of the cutting edge 26 as described previously herein). In some embodiments, the offset Y may be reduced in order to decrease the shearing force or the offset Y may be increased in order to increase the shearing force. More particularly, the length of the slot 32 within the inner member 20 with may be adjusted in order to alter the position of the cutting edge 26. In a specific example, the cutting edge 26 may be positioned adjacent to the distal end face 25 of the inner member 20 increasing the offset Y. As a result, a greater force may be exerted by the outer member 10 as it is advanced over the inner member 20, thus increasing the shearing force that is generated between the inner and outer members 20, 10. Alternatively, the cutting edge 26 may be positioned adjacent the bend 23, resulting in a reduced vertical offset Y and thus a smaller x value. This may reduce, for example, the deflection of the outer member 10 and the inner member 20, as the outer member is advanced over the inner member 20. A smaller deflection equates to a lower applied spring force (and thus a lower k-value of the assembly 100), and this may result in lower shear force being generated between the inner and outer members 20, 10.

As discussed above, in some embodiments the amount of shearing force or shear force that is generated is governed by the k-value or spring constant of the system, which may be modified in order to adjust the amount of force that is used to cut the suture. In some such embodiments, the k-value of the system is dominated by the minimum k-value or spring constant. In other words, the k-value of the weaker or the softer member governs the k-value of the system. In a particular example of this, the k-value of the system is dominated by the k-value of the outer member 10 (which is relatively weaker than the inner member 20) with the k-value being defined by the diameter or wall thickness of the outer member 10 for a given material. Some such embodiments of the present invention provide a suture cutter comprising a solid outer member 10 (i.e. cut-outs or openings are not provided within the outer member) which allows the k-value of the outer member to be maximized and hence allows the shearing force to be maximized and provides a consistent shearing force.

More specifically, the k-value of the suture cutter assembly 100 is determined by the combined k-values of the outer member 10 and the inner member 20. In some embodiments, the k-values of each of the inner and outer members 20, 10 are dependent on length, material and geometry. In one specific example, k-value may be determined using a beam deflection equation for an end loaded cantilever beam where the displacement $Y=FL^3/3EI$. For some embodiments of the present invention, $F_{shear}$ can be defined as being equal to $3EI/L^3$ Y, where the displacement Y refers to the vertical displacement or offset as outlined herein above and the k-value is equal to $3EI/L^3$ a]. The k-value is the spring constant and is a measure of stiffness. In a particular example, the k-value of the suture cutter assembly can be viewed as the combined k-value of two springs in series where K1 and K2 refer to K-values of the inner and outer members 20, 10 [F~(K1)(K2)/(K1+k2) x, where x is equal to the vertical displacement or offset Y]. In such systems where spring constants are positioned in series with each other, the weaker of the two individual k-values of the springs dominates and determines the combined k-value of the assembly or system 100. The shearing force generated by the system 100 is then proportional to the combined k-value of the system 100. Thus, in accordance with an embodiment of the present invention, a weaker member is provided that comprises a much lower k-value than the other member, allowing the k-value of the system 100 to be dominated by the weaker member. In one such embodiment the outer member may be of a lower stiffness than the inner member 20 and as such the k-value of the outer member 10 for example K1 may be lower than a k-value of the inner member for example K2. As such the k-value of the outer member 10 dominates and substantially determines the k-value of the system. As such, any changes in the inner member 20 will not dominate the behavior of the system in terms of stiffness and may have a negligible effect on the k-value of the system. Since the k-value of the outer member 10 dominates it is a measure of the k-value of the system as well its stiffness. This may provide a substantially robust system as it is largely dependent on a single control variable or in other words the k-value of the outer member 10. This may allow the device in accordance with an embodiment of the present invention to predictably provide sufficient force in order to cut suture where changes in the inner member 20 may not affect the force provided by the system. In a particular embodiment, an outer member 10 is provided that is weaker than the inner member 20, where the k-value of the outer member 10 dominates and determines the k-value of the system 100. The k-value of the outer member 10 may vary substantially, or in other words, may have a value that is orders of magnitude apart from the k-value of the inner member 20. Since, the k-value of the outer member 10 is determinative of the k-value of the system 100; as such the k-value of the outer member 10 may be modified to control the desired k-value of the system 100. In one such example, a solid outer member 10 is provided which provides a consistent k-value for the outer member 10 and the system or assembly 100 and as such allows the system to behave predictably. Furthermore, the solid outer member 10 may allow the k-value of the outer member (which is the weaker member and the member whose k-value dominates) to be maximized in order to maximize the k-value of the system. As a result a sufficient amount of force may reliably be provided by the suture cutter assembly 100 in order to cut the suture.

In a particular example of this, the outer member 10 is provided as a solid outer tube (i.e. a tube that lacks cut-outs or windows). The solid outer tube results in low manufacturing tolerances and hence provides a repeatable outer member 10 with a substantially consistent k-value and thus shearing force. In other words tolerance is minimized.

in the dominating member that dominates the k-value of the system (i.e. the outer member 10) in order to provide a consistent k-value for the system 100. Additionally, manufacturing tolerances or changes in dimensions of the inner member 10 will not have a significant impact on the resultant combined k-value of the system, as the determinative k-value is that of the outer member 10. As a result the output force generated by the system 100 and experienced by the user is substantially consistent. Furthermore, the solid outer tube maximizes the k-value of the outer member 10 and thus the system 100 by eliminating slots or cut-outs within the outer member 10 and/or by reducing manufacturing tolerances as discussed above, which may help maximize the shearing force generated. Thus, in accordance with an embodiment of the present invention, providing a solid outer member 10, results in a system 100 where the k-value of the outer member 10 (and as a result combined k-value of the system 100) is repeatable and maximized to provide a consistent output shearing force that is sufficient for cutting the suture.

In other embodiments, the k-value of the inner and outer members 20, 10 may be substantially the same or matched. In other words, the k-values of both the inner and outer members 20, 10 may be substantially of the same order of magnitude. As a result the inner and outer members 20, 10 may displace by substantially the same amount, and the maximum displacement of each of the inner and outer members 20, 10 may be minimized. In some such embodiments, where the inner and outer members 20, 10 comprise stainless steel, minimizing displacement of the inner and outer members 20, 10 may allow both the inner and outer members 20, 10 to remain in the elastic region. Additionally, providing a solid outer member 10 provides a substantially consistent k-value of the outer member 10 (as discussed in the previous embodiment) which may reduce the susceptibility of the system to changes in k-values resulting from modifications within the inner and outer members 20, 10. Thus, the solid outer member 10 may contribute towards a substantially consistent combined k-value of the system 100, which further results in a consistent shearing force to be generated by the system 100 and applied to the suture. Furthermore, the shearing force may be maximized as the solid outer member 10 may provide a maximized k-value for the outer member 10 for the given embodiment. In accordance with an embodiment of the present invention the k-value of the outer member 10, for example K1 may be equal to about 3.3 times the k-value for example k2 of the inner member 20. In some embodiments, such a system may provide flexibility in terms of modifying the inner and the outer members 20, 10 as changing either the inner or the outer members 20, 10 may not substantially impact the force generate in order to cut the suture.

In still other embodiments, the inner member 20 may be weaker or softer than the solid outer member 10 and may have a k-value that is lower than that of the outer member 10. As a result the k-value of the inner member 20 may dominate and determine the combined k-value of the system. As such, the inner member 20 may be modified in order to control the k-value of the system and thus the shearing force. More particularly, in one such example, the k-value or spring constant of the inner member 20 is defined by the dimensions of the slot 32, which may be altered to modify the k-value. In some such embodiments, a solid outer member 10 may be provided that is substantially stiffer and more rigid than the inner member 20. In some such examples, a system or assembly 100 is provided where the k-values of the weaker inner member 20 and the outer member 10 may be orders of magnitude apart. In such embodiments, the stiffer solid outer member 10 ensures that a consistent difference is provided between the magnitudes of k-values of the inner member 20 and the outer member 10, thus ensuring that the k-value of the inner member 10 dominates and thus determines the combined k-value of the system 100.

As such any variations in the solid outer member 10 do not substantially influence the combined k-value of the system 100. As a result the combined k-value of the system 100 may be altered by changing the parameters of the inner member 20 independently from the outer member 10. Furthermore, providing a solid outer member 10 that is substantially stiffer than the weaker inner member 20, may allow the combined k-value of the system 100 to be maximized by altering the k-value of the inner member 20 independently from the outer member 10. Therefore, the solid outer member 10 may be part of a system that provides a consistent k-value for the inner member 20 (which defines the combined k-value of the system 100) in order to provide a consistent output shearing force that is maximized to be sufficient for cutting the suture.

In another example, the k-value of the system may be adjusted by changing the angle w of the bend 23 (with reference to the device longitudinal axis A-A, as shown in FIG. 3A). If the angle w of the bend 23 is reduced, the vertical offset Y is reduced. As a result a lower displacement Y is required for the outer member 10 to interact with the inner member 20, which in turn reduces the shearing force that is generated between the two members. Alternatively, if the angle w is increased, the vertical offset Y is increased. As a result a greater displacement Y is required for the outer member 10 to interact with the inner member 20 and hence a greater shear force is generated between the inner and outer members, 20, 10. In one such example, instead of increasing the angle w, the length of the tip 24 of the inner member 20 may be increased with the angle w being kept the same in order to provide the same greater displacement Y. The user may have to advance the outer member 10 for a longer distance over the inner member 20, in order to provide the same greater displacement Y. Thus, this may provide the same displacement Y with the unchanged or shallower angle, and as such may provide less frictional force. Thus, the user may experience less resistance as force is applied by the user to actuate the suture cutter 100 to advance the outer member 10 over the inner member 20. In other words, a shallower angle w with a longer distal tip 24 provides a decreased normal component to the applied force, and in turn reduces the frictional component that is dependent on the normal component of the force applied. As a result, there is less frictional loss experienced which reduces the applied force that is required by the user in order to provide the same shear force.

In another example, the lateral width of the slot 32 within the inner member 20 may be adjusted to control the spring constant or the k-value of the system. If the lateral width of the slot 32 is increased, the flexibility or spring within the inner member 20 increases. This provides a lower k-value which results in a reduced shear force being generated between the inner and outer members 20, 10.

In some such embodiments, as described herein, the side slot 32 has a lateral width which allows varying number of sutures and/or multi-filament sutures to be accommodated within the inner member 20 without substantially affecting the k-value of the system. In other words, the k-value of the system and the shearing force are not altered substantially during use as additional sutures are added and held within the device 100. In still a further example, the outer diameter (OD) of the inner member 20 may also be maximized to assist in accommodating the multi-filament and/or multiple sutures without affecting the k-value of the system.

Furthermore, with reference again to FIG. 2F, in some embodiments the k-value of the inner member 20 may be altered by changing the angle of the distal tip 24 such that the top edge or surface t of the inner member 20 is not parallel to the bottom edge or face b of the inner member 20. This may provide a means to modify the k-value of the inner member 20 and thus the combined k-value of the system 100 by reducing material within the inner member 20. Still furthermore, in some embodiments as discussed herein above the inner member 20 comprises a solid member that comprises a solid bent rod. The solid inner member 20 provides a greater tolerance when hardened during a hardening process and as such, the stiffer inner member 20 may be less susceptible to tolerances and may not affect the overall k-value of the system 100 which may be dominated by the weaker outer member 10.

Furthermore, as an additional feature, the shearing force may not be affected substantially by adjustments made to the tail length of the cut suture. In other words, the tail length of the cut suture may be controlled independently from the shearing force. More specifically, in some embodiments as shown in FIG. 2F, the angle S of the under-cut or inside edge 27 defines the cut length of the suture tails or the tail length. Thus, the tail length may be controlled by adjusting the length and angle S of the under-cut 27, which affects length c of the under-cut 27 that corresponds to the tail length. This may be done without altering the dimensions of the slot 32 and hence without affecting the shearing force. In some such examples, the angle S may be reduced to increase the tail length or alternatively angle S may be increased to reduce the tail length. Furthermore, in some such embodiments, the outer diameter (OD) of the inner member 20 may additionally be maximized while maintaining a constrained OD of the device to allow for a maximum tail length. Furthermore, adjustments may be made to the tail-length by altering or modifying the inner member 20 distal to the cutting edge 26. These modifications made distal to the cutting edge 26 may not affect the k-value of the inner member 20 and thus the system 100. In some such embodiments, the bottom edge or surface of the inner member 20 may be modified as shown by b' such that the length c of the under-cut 27 is shortened to provide a shorter tail length. In some such embodiments the bottom edge or surface b' may allow for a shorter tail length than the diameter of the inner member 20 allows for. In the particular example shown, the bottom edge b' is provided as a chamfered face/cut that is substantially perpendicular to the under-cut or inside edge 27.

Thus, in accordance with some embodiments of the present invention, a suture cutter 100 is provided with a solid outer member 10 and a curved inner member 20 comprising a bend 23 and a lateral or side slot 32 to accommodate multi-filament and/or multiple sutures, whereby interference is provided between the two members to cut the multi-filament and/or multiple sutures. The k-value of the system (which is governed by the weaker of the two members) is maximized in order to allow the system to generate sufficient shearing force upon actuation to cut the multi-filament and/or multiple sutures.

Method of Cutting Suture

Additional embodiments of the present invention comprise a method of cutting suture, the method comprising: loading a suture through a side passage of an inner member of a suture passer and moving at least one of the inner member and an outer member of the suture passer relative to the other of the inner member and the outer member such that an exit from the side passage is obstructed by the outer member, thereby preventing the suture from exiting through the side passage. These embodiments may additional comprise advancing the suture passer along the suture to a desired cutting location, and moving at least one of the inner member and outer member relative to the other of the inner member and outer member to cut the suture at the desired cutting location.

Figure 4A:
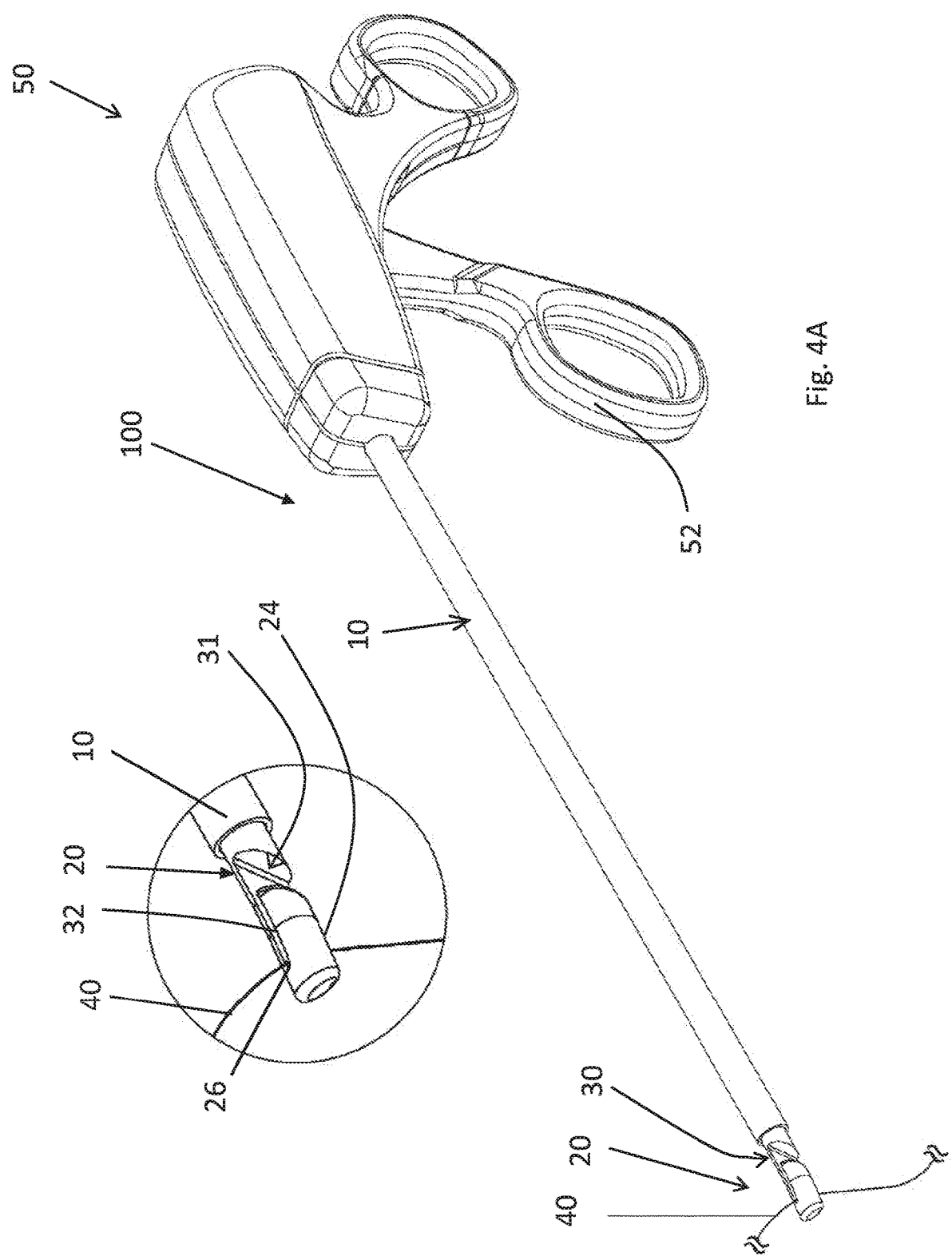
FIGS. 4A-4C illustrate a method of using the suture cutter in accordance with an embodiment of the present invention.
Figure 4B:
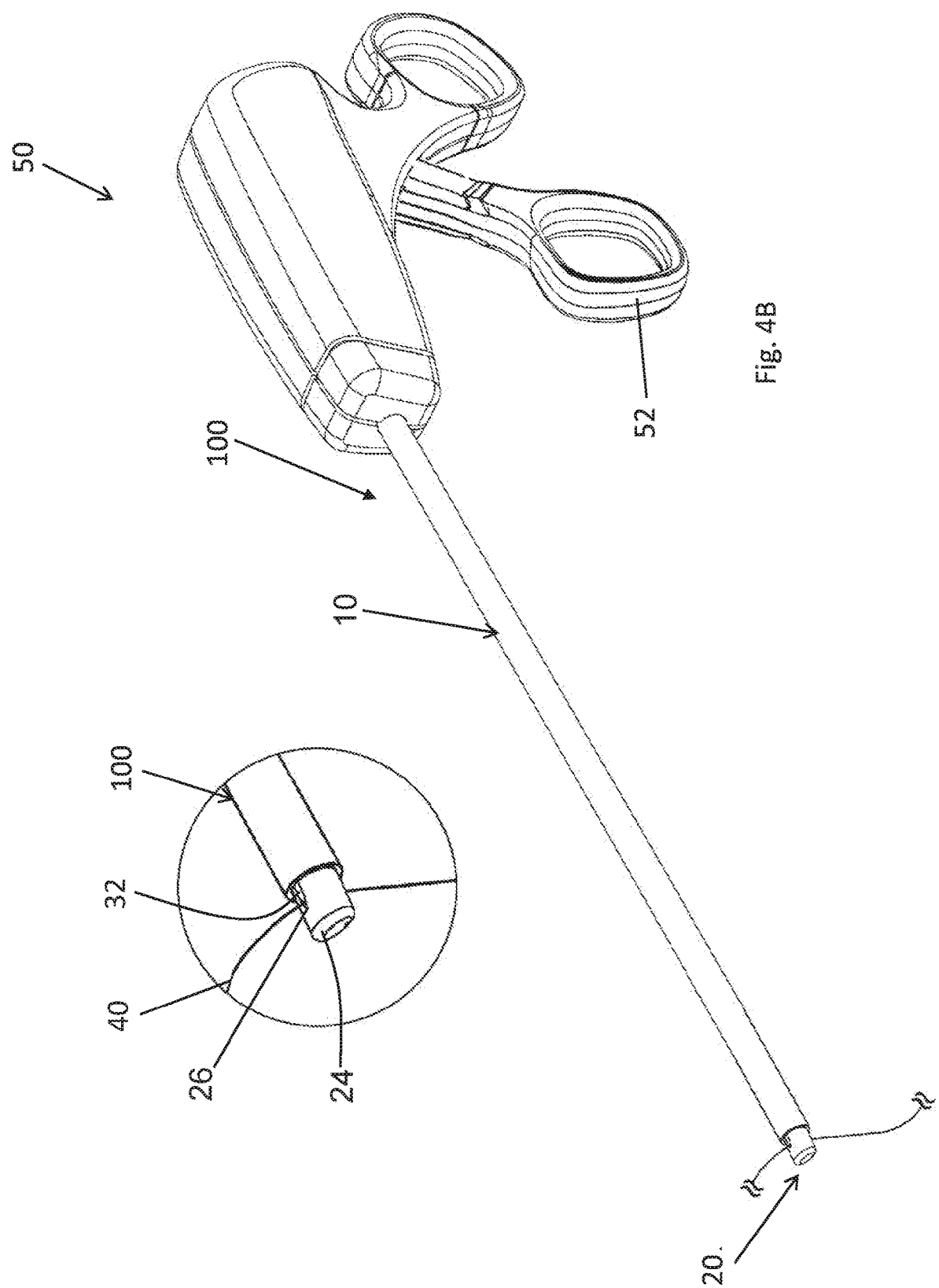
Figure 4C:
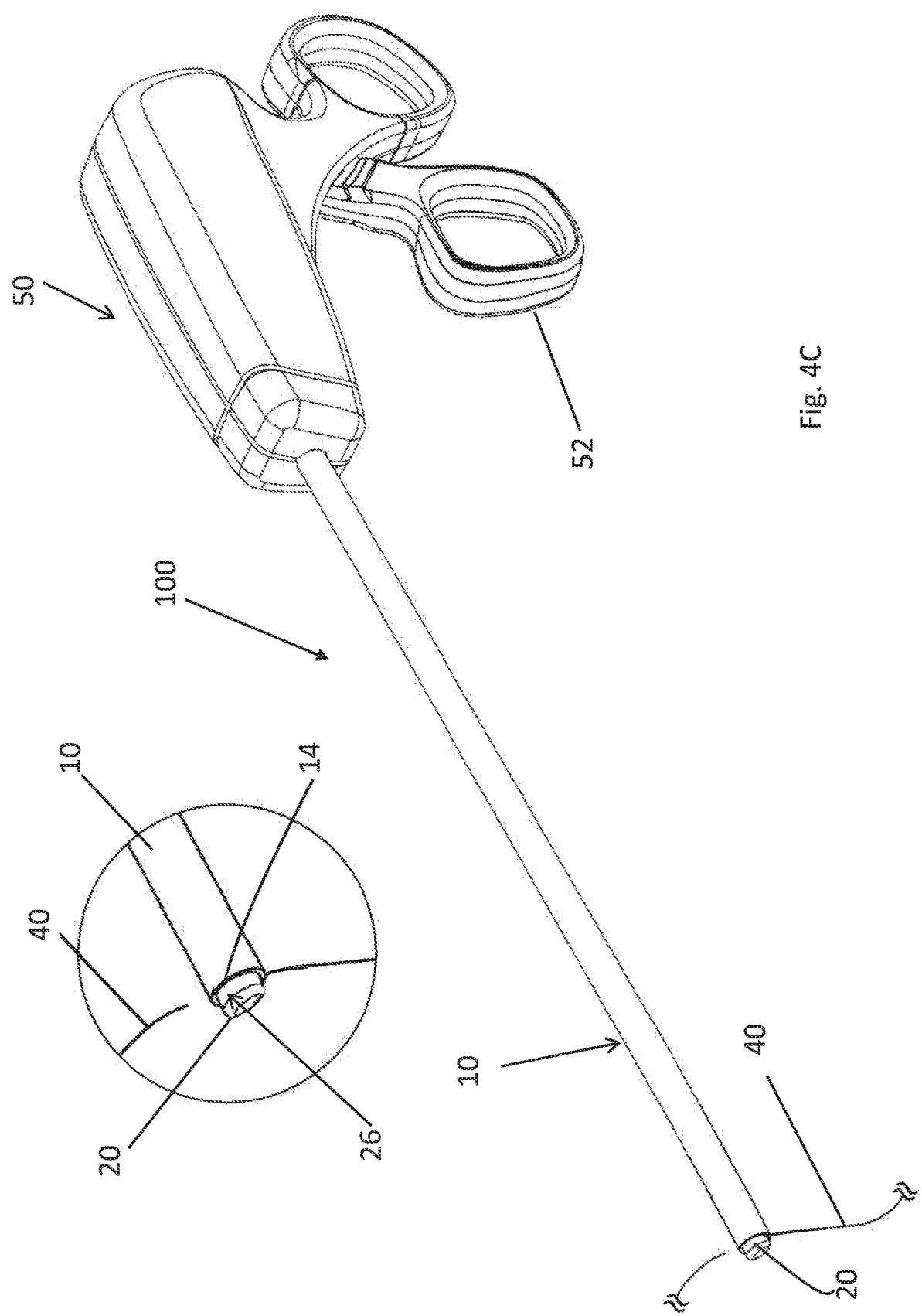

For example, with reference now to FIGS. 4A-4C, a method of cutting suture is shown, using device 100. As shown in FIG. 4A, a suture is 40 is received through passage 31 and into the slot 32 of the opening 30 and initially the slot 32 remains open. The suture 40 is held against the cutting edge 26. The trigger 52 is then actuated to linearly translate or advance the outer member 10 in a distal direction over the distal tip 24 of the inner member 20. As the trigger 52 is actuated further allowing initial advancement of the outer member 10, as shown in FIG. 4B, the passage 31 and slot 32 are now partially enclosed or covered by the outer member 10 but the suture 40 has not been cut. The suture loading and retaining slot 32 is located at 1 east partially within the lumen of the outer member 10 to provide rigidity at the point of cutting. Since, the passage 31 into the slot 32 is sealed by the outer member 10 this additionally helps to retain the suture 40 within the slot 32. This may allow the suture cutter 100 to capture the suture 40 within the slot 32 without cutting it and may allow the physician to advance the suture cutter 100 with the suture 40, without losing the suture 40.

With reference now to FIG. 4C, as the trigger 52 is actuated or pulled further, the outer member 10 is advanced over the inner member 20 such that interference is created between an inner edge 14 at the distal end of the outer member 10 and the inner member 20 at the cutting edge 26 (at the point where the suture 40 is held) in order to cut the suture 40. As outlined previously, the cutting edge 26 at the slot 32 is initially at a vertically offset position with respect to the device longitudinal axis or axis B-B and the distal tip 24 defines an angle or bend or curve 23. This allows the inner member 20 to be co-axially offset or simply offset from the outer member along the bend or curve 23. As the outer member 10 is advanced over the inner member 20, the inner member 10 tries to straighten out and the outer surface of the distal tip 24 along the slot 32 is forced against the inside of the outer member 10, creating a shearing force which creates the cutting mechanism for cutting the suture 40. Furthermore, due to interference created between the outer and inner members 10, 20, the inner member deflects inwards towards the device longitudinal axis A-A. More specifically, interference is created between the inner surface of the outer member 10 (specifically, at the leading edge 14) and the cutting edge 26 of the inner member in order to cut the suture 40 held there-between. The mechanism of cutting suture 40 is described further herein-below with reference to FIG. 4C.

Since the device 100 of the present invention permits minimum flexion or bending of the inner and outer members 20, 10 due to the rigidity of the inner and outer members 20, 10, a significant amount of shearing force is generated to cut the suture 40. Furthermore, the rigidity of the solid outer member 10 prevents the outer member 10 from sliding over and past the inner member 20 without cutting the suture 40. The rigidity of both the inner and outer members 20, 10 thus results in minimal flexion of the system as a whole and ensures that the shearing force is sufficient for cutting.

With reference again to FIG. 2F, in some embodiments, the flexion or deflection of the outer member 10 at the cutting edge 26 may range from be from between about 0.013" to about 0.017" (or about 0.33 mm to about 0.43 mm). In one example, the deflection of the outer member 10 is equal to about 0.015" (0.36 mm). In other words the outer member 10 deflects up [for example away from the longitudinal axis C-C] due to the curve of the inner member 20 such that the vertical displacement of the outer member 10 at the cutting edge 26 is equal to about 0.015". In some embodiments, the inward deflection of the inner member 20 (or vertical displacement of the inner member 20 at the cutting edge 26 towards the longitudinal axis C-C) is observed to be about 0.004" (0.10 mm). The deflection of the inner member 20 may function as a parameter for indicating the rigidity of the outer member 10. Increased rigidity of the outer member 10, results in greater deflection of the inner member 20 as the outer member 10 is advanced over it. Therefore, the deflection of the inner member 20 can be viewed as an outcome of the rigidity of the outer member 10.

In some embodiments, the deflection of inner member 20 is used to determine a 'deflection to base line value' or DBL which indicates the rigidity of the outer member 10 and additionally of the system as a whole (the system being formed by the combination of the inner and outer members 20, 10). The deflection to base line value (DBL) is calculated as a ratio of this observed deflection at the cutting edge 26 over the total available deflection (which is defined by the vertical offset of the cutting edge 26 measured with reference to the longitudinal axis C-C which is alternatively referred to as base line C-C, as shown in FIG. 2F).

The base line C-C is defined as the point the cutting edge 26 would reach if there was 100% deflection of the inner member 20. In other words, it is the point at which there is complete theoretical deflection of the inner member 20 due to the advancement of the outer member 10 over it, resulting in the straightening of the curvature of the inner member 20. In some embodiments, the baseline C-C is positioned at between about 0.120" to about 0.130" from the axis defined by the bottom edge of the inner member 20. In some such embodiments, the total available deflection or the offset Y of the cutting edge 26 from this base-line C-C is equal to between about 0.012" to about 0.026". In other words the cutting edge 26 is vertically offset by a distance of between about 0.012" to about 0.026" from a longitudinal axis extending along an upper edge or top edge of the inner member 20. In one specific example, the cutting edge 26 is initially located at an offset Y of about 0.019" from the base-line C-C.

In one embodiment, as the outer member 10 is advanced over the inner member 20, the observed or actual deflection of the inner member 20 (measured at the cutting edge 26) towards the base-line C-C is equal to about 0.004" (0.10 mm). In some embodiments, the displacement to base line of the inner member is between about 15% to about 33%. In a specific example, the DBL value is calculated to be about 0.004/0.019 which is equal to about 21%. In the embodiment described, the deflection of the inner member 20 by at least about 15% indicates an outer component having a sufficient rigidity so that a sufficient shearing force is generated at the cutting edge 26 in order to cut suture. In some such embodiments, increased deflection of the inner member 20 may indicate increased rigidity of the outer member 10 and increased shearing force to effectively cut the suture 40. Thus, in the particular example discussed and shown in FIG. 4C, as the trigger 52 is actuated, the inside leading edge 14 of the outer member 10 is brought along the same plane as the suture 40 and the cutting edge 26 at the point of cutting. This interference deflects the inner member 20 down [towards for example axis B-B of FIG. 2F] and allows the suture 40 to be cut by the shearing force that is generated. In some such embodiments, as described above, the inner member 20 may be deflected such the deflection to baseline (DBL) of the cutting edge 26 is at least about 15%. In some embodiments, the outer member 10 may have a DBL value that is less than about 85%. In a specific example, the vertical displacement of the outer member 10 is equal to about 0.015". As a result in one example, the DBL value of the outer member 10 may be about 0.015/0.019 which is equal to about 79%. In some embodiments, the outer member is sufficiently stiff that it substantially does not deflect such that the DBL value is about zero.

With reference again to FIG. 4C, the cutting mechanism of device 100 upon actuation is described further with reference to additional features of the device. In some embodiments, the available surface area (SA) of the slot 32 at the cutting edge 26 tapers down to one suture diameter (FIGS. 2D, 2E). In some embodiments, the cutting edge 26 tapers down to less than one suture diameter while preventing pinching and in some examples may allow the suture to be held therein in a flattened configuration. As discussed with reference to FIG. 4C, as the trigger 52 is actuated and leading inner edge 14 of the outer member 10 is advanced at the cutting edge 26, in embodiments where a multifilament suture 40 is being cut (for example a UHPE suture), the reduced SA at the cutting edge 26 may prevent bending of the suture fibers and may prevent the individual strands of the multifilament suture 40 from flattening out to reduce the surface area of the suture 40 to enable effective cutting. The suture fibers remain in the confined space at the cutting edge 26 and the interference force thus the shear force is exerted over a small surface area providing increased pressure for cutting the suture 40.

In some embodiments, additional features may be provided on the cutting edge at the slot 32 to further enhance cutting, such as providing angles on the cutting surface at the cutting edge 26. As the leading inner edge 14 of the outer member 10 is advanced against the suture 40 and cutting edge 26 the interference between the inner and outer members 20, 10 generates pressure in the confined space at the cutting edge 26, that is sufficient to enable cutting of the suture 40. The force applied or exerted is increased while providing a decreased surface area (against which the force is applied) in order to cut suture 40. Furthermore, the undercut 27 below the edge portion 28 of the inner member 20 provides a cutting edge 26 that is able to reach or exert pressure against the suture 40 that is sufficient for cutting. In one example, the under-cut 27 is perpendicular to the cutting edge 26. Furthermore, in the particular example shown, the suture 40 may be less likely to curve around the cutting edge 26 and sits against it, which may additionally assist in cutting the suture 40. In some embodiments the cutting edge 26 may be formed such that it may allow the device or suture cutter 100 to be used multiple times while still providing effective cutting along the cutting edge 26. In some such examples the cutting edge 26 may not require sharpening prior to multiple uses.

In some embodiments, features may be provided to prevent binding of the device 100 as it is actuated to cut the suture 40. In one embodiment, the inner member 20 may be trimmed back or down in the region distal to the cutting edge 26. In other words, the length of the edge portion 28 (FIGS. 2F and 2E) may be shortened to prevent binding. In one example, the length of the curve or bend 23 or the length of inner member distal to the curve or bend 23 may be reduced to help prevent binding. In other embodiments, the actuation distance of the outer member or cannula 10 may be altered to prevent binding. In a specific example of this, the outer member 10 is only permitted to travel a known distance with respect to the curve or bend 23 to help prevent binding while still allowing the suture to be cut. The location of the cutting edge 26 and the slot 32 may be adjusted to enable the device 100 to cut suture 40 upon actuation of the trigger 52. The outer member 10 may only be advanced until it cuts the suture 40. In still other embodiments as outlined previously, the distal tip 24 is provided with a bend angle (or curvature) that is between about 6 to about 8 degrees with the cutting edge offset being from 0.0142" to about 0.0146" (from the lower edge of the device proximal portion) to help prevent binding. The suture cutter or device 100 may be provided in various sizes and/or materials and may still provide a sufficient tensile strength that is required for cutting suture 40 while preventing binding.

In some embodiments, the apparatus or suture cutter 100 may be used to cut suture strands or suture tails of a suture knot. In one such example, where the device 100 is used during a surgical procedure to cut the suture tails of a knot, the distal end face 25 of the inner member 20 (FIG. 2F) may be pressed against the knot and the free ends of the suture may be inserted through the opening 30 and held within the slot 32 and positioned against the cutting edge 26. The suture tails are routed such that they exit the knot and enter the slot 32 from the bottom of the slot 32. The suture tails are placed against the under-cut 27 (FIG. 2F), and exit from the top of the slot 32. The distance between the bottom of the slot 32 to the top of the slot 32 along the under-cut 27 defines the cut length of the suture tails or the tail length. The suture cutter 100 may then be actuated to cut the suture tails.

Figure 5A:
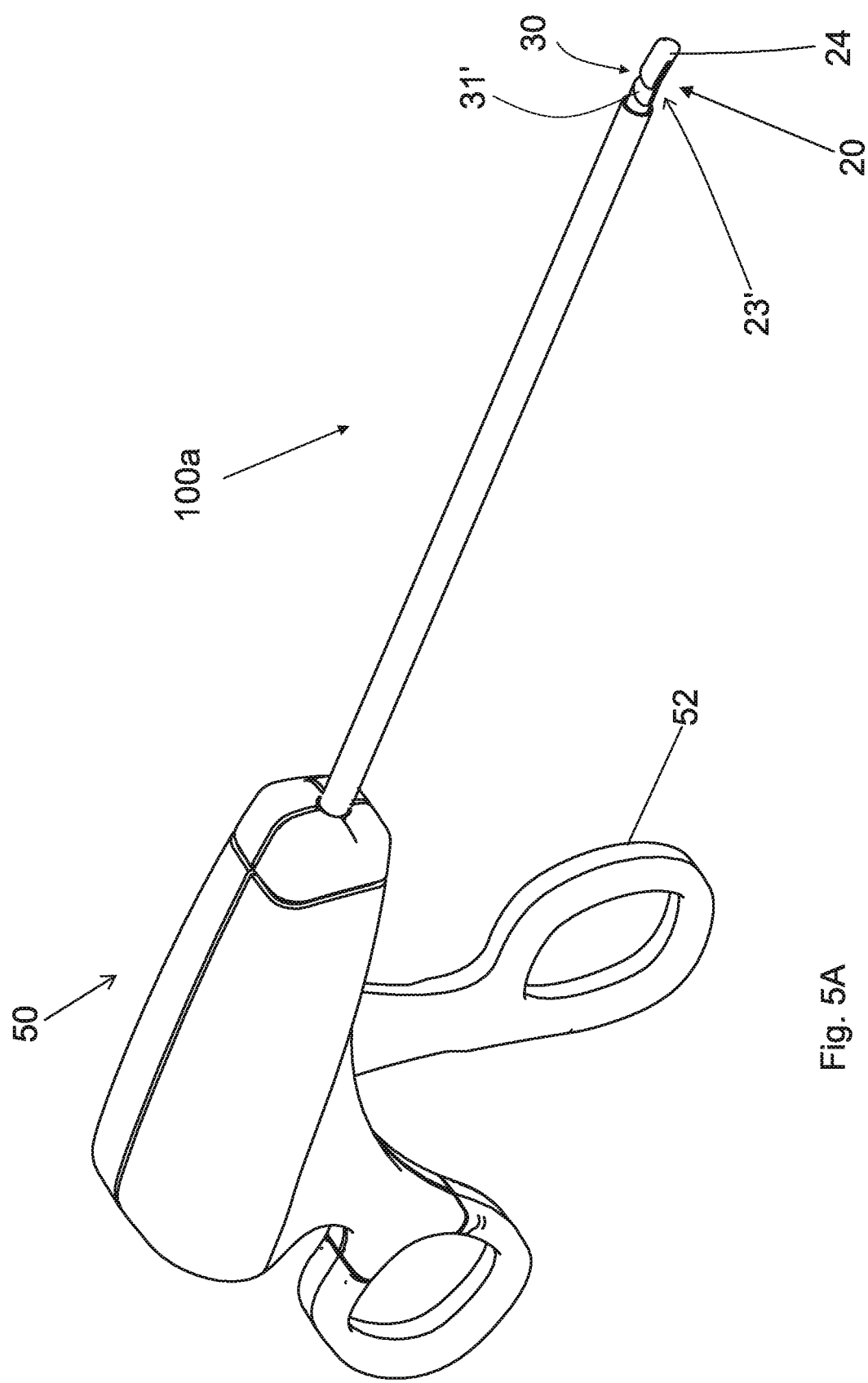
FIGS. 5A and 5B illustrate perspective views of a suture cutter with a reverse bend in accordance with an alternate embodiment of the present invention.
Figure 5B:
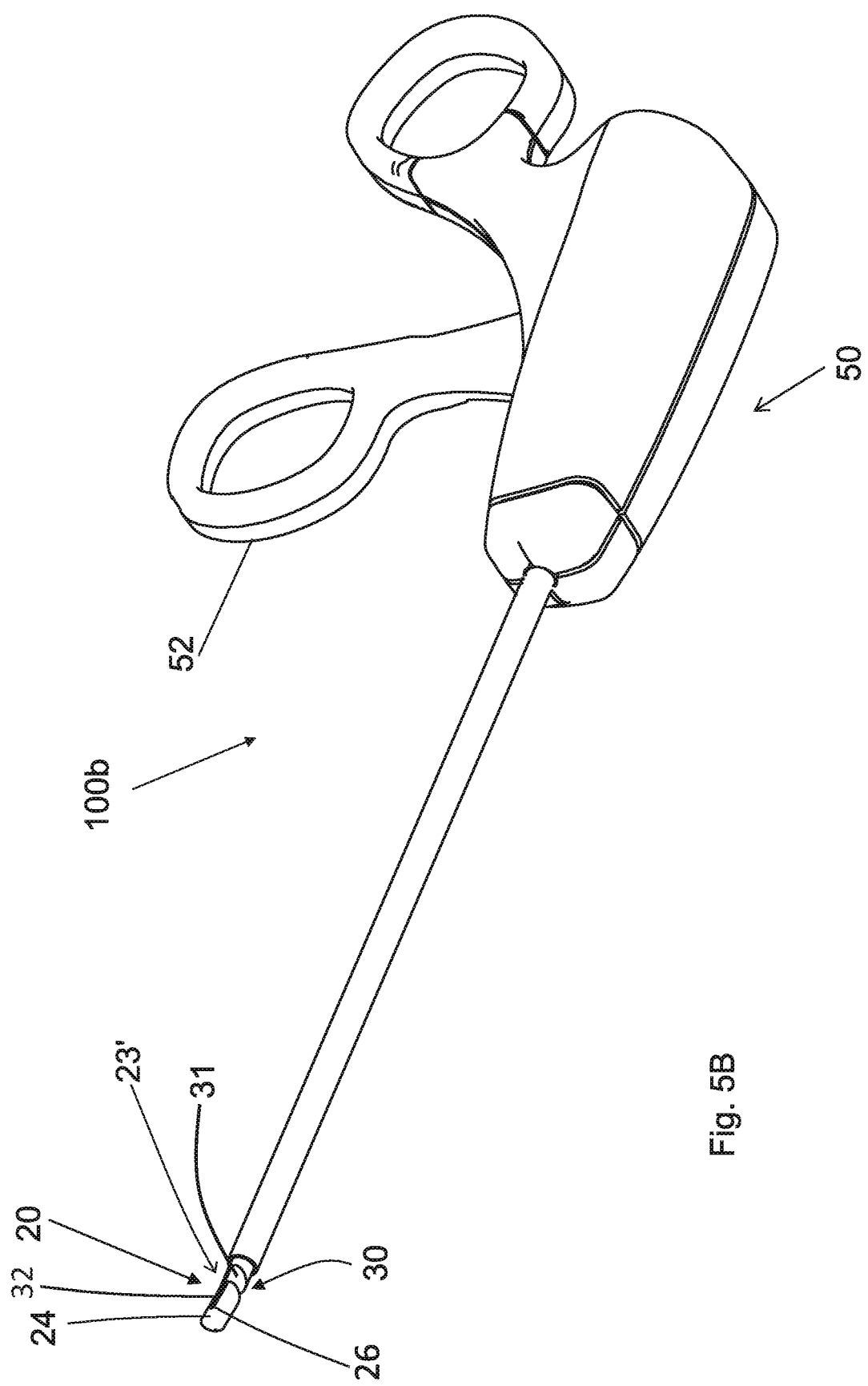

As discussed previously in some embodiments as shown in FIG. 1A, the distal tip 24 is bent or curved upwards away from the bottom end of the device 100. In an alternate embodiment of the present invention, as shown in FIG. 5A and FIG. 5B, a device 100a is provided with an alternate configuration where the distal tip or portion 24 of the inner member 20 is curved or bent downwards forming a reverse bend 23' that is oriented at an angle of 180 degrees compared to bend 23 in device 100 of FIG. 1A. Similar to embodiments discussed herein-above, the distal tip 24 may be bent away from the longitudinal axis at angle of about 6 to 8 degrees, defining a distal tip curvature. The reverse bend 23' enables use of the device 100a in an alternate configuration during use. More specifically, the reverse bend 23' allows the device 100a to be used in an upside down configuration or orientation. In order to use the device 100a, the physician may orient the handle housing 50 in its flipped configuration, for example, by rotating it along its longitudinal axis by 180 degrees. Once in this flipped upside down configuration, as shown in FIG. 5B, the curve or bend 23' along the distal tip 24 of the inner member 20 faces upwards. Thus, the bend 23' is now oriented in the same direction as bend 23 of device 100, that is shown in FIG. 1A. Similarly, cutting edge 26 remains facing upwards with the passage 31 defined by the opening 30 remaining on the left hand side of the device 100a. The device may now be used in a similar fashion as before. In some such embodiments, the device 100a may be used to cut suture strands 40 that exit a knot. The knot may be positioned within groove 34 within the distal tip or portion 24 of the inner member 20 (shown in FIG. 3C) such that the suture strands 40 that exit the knot are inserted through opening 30. The suture strands 40 are then guided into slot 32 which defines a cutting region comprising the cutting edge 36 to be positioned at the cutting edge 26.

Similar to embodiments discussed herein above, the trigger of device 100a may then be actuated to enable relative movement between the outer member 10 and the inner member 20 in order to cut the suture strands 40. As the trigger is actuated, the outer member 10 is advanced over the curved inner member 20, the leading inner edge 14 of the outer member 10 is pressed against the suture 40 and cutting edge 26 such that interference is created between the inner and outer members 20, 10. This interference generates pressure in the confined space at the cutting edge 26 that is sufficient to enable cutting of the suture 40. Thus, even though the device 100a is held upside down the knot is not positioned at the cutting surface or cutting edge 26 but rather away from the cutting surface or cutting edge 26, which enables the physician to cut the suture strands 40 to form suture tails while ensuring that the knot construct remains secure and undamaged. As such, some embodiments of the present invention provide a device 100a that may be held upside down during use based on the physician's preference.

Figure 5C:
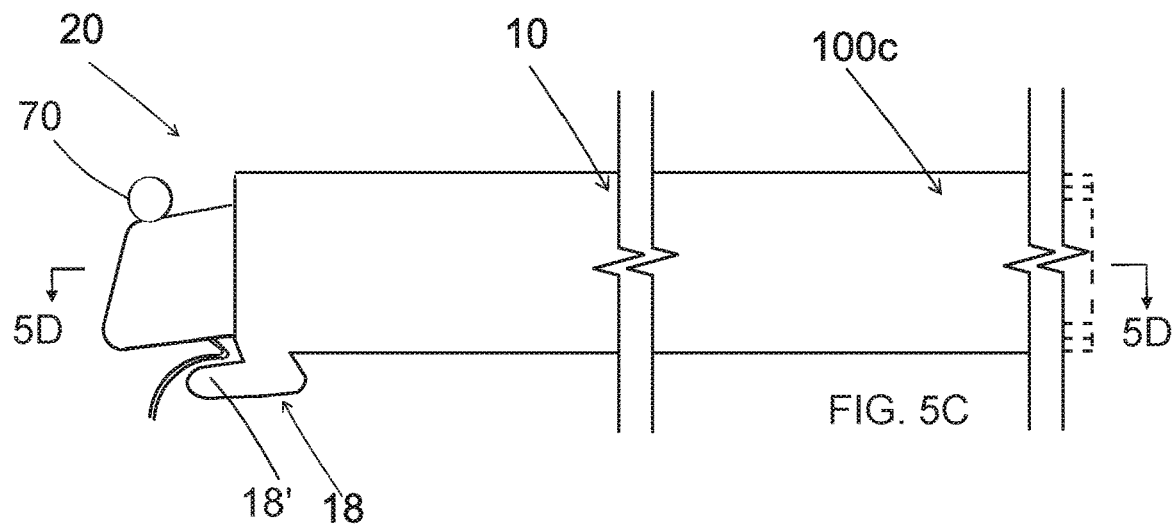
FIG. 5C illustrates a side view of a distal end of a suture cutter of the present invention in an upside down configuration illustrating a guiding flange in accordance with an alternate embodiment of the present invention.
Figure 5D:
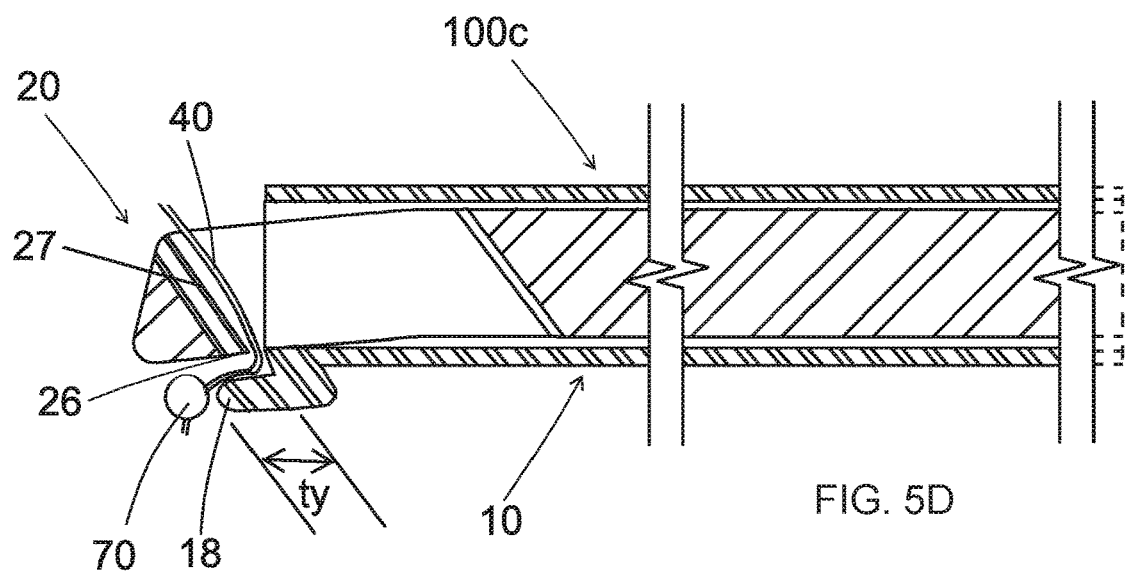
FIG. 5D illustrates a cross-sectional view of the suture cutter of FIG. 5C taken along line 5D-5D of FIG. 5C, in accordance with an embodiment of the present invention.
Figure 5E:
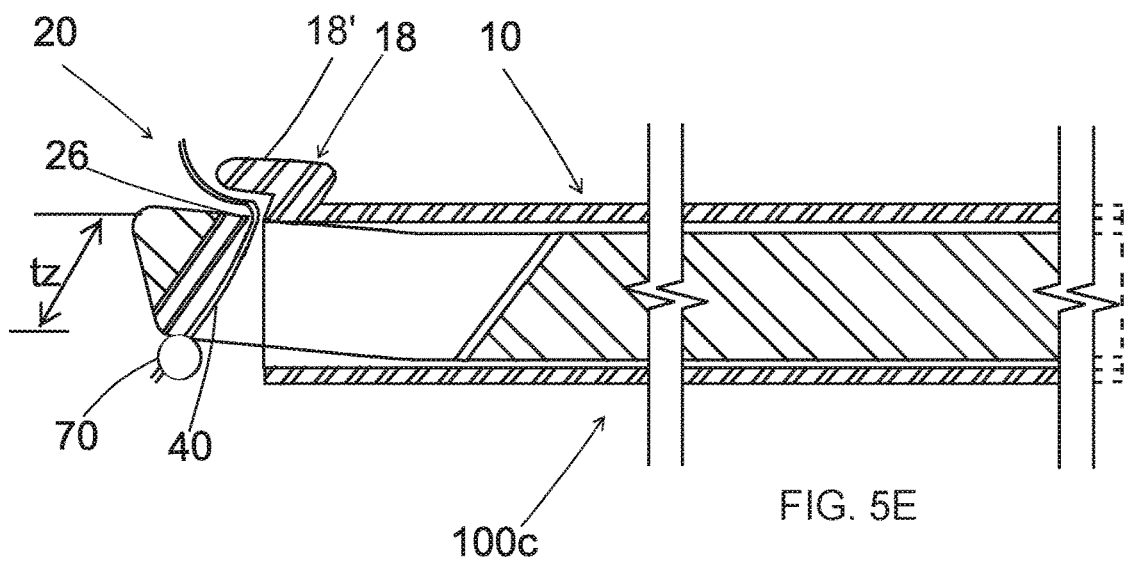
FIG. 5E illustrates a cross-sectional view of FIG. 5D shown in an upright configuration, in accordance with an alternate embodiment of the present invention.

In additional embodiments of the present invention, as shown in FIG. 5C, a distal portion of a device 100c is shown, that comprises a feature that enables multi-configurational use of the device by providing a number of rotational configurations for example in either an upside down configuration or the upright or nominal configuration, without damaging the knot while providing a sufficient tail length to prevent unravelling of the knot. In the embodiment illustrated in FIG. 5C, an outer member 10 comprises a guiding flange 18. When the device is held in an inverted or upside down configuration or orientation as shown in the cross-section shown in FIG. 5C and the cross-sectional view shown in FIG. 5D [similar to the embodiment shown in FIG. 5B], the guiding flange 18 functions to guide and distance the knot 70 away from the cutting edge 26 in order to provide a tail length ty. In other words, in this flipped or inverted configuration, the guiding flange 18 pushes the knot 70 away from the cutting edge 26 to prevent the knot from being cut and/or to prevent a very short tail length from being formed which could result in unravelling of the knot 70. Additionally the guiding flange 18 by pushing the knot 70 also provides a tail length that is equal to the length of longitudinally extending portion or arm 18' of the guiding flange 18, that extends beyond the leading edge 14 of the outer member. In other words the tail length is equal to the distance between the distal portion of the guiding flange 18 and the cutting edge 26. Thus, in some embodiments, the flange 18 allows for a tail length of a sufficient size to be cut, in order to prevent unravelling of the knot 70. Therefore, the tail length may be defined as a function of the guiding flange 18 and the guiding flange may be adjusted in some embodiments to provide varying tail lengths. Furthermore, as illustrated in FIG. 5E, the device 100c may additionally be used in the upright configuration, similar to the example shown in FIG. 1A. The device 100c may allow suture to be placed through the slot 32 such that the tail length tz is defined by the under-cut 27 as shown. Alternatively, in some embodiments, the guiding flange 18 may be positioned adjacent the cutting edge 26 of the inner member, for example distal to the cutting edge 26.

Figure 5F:
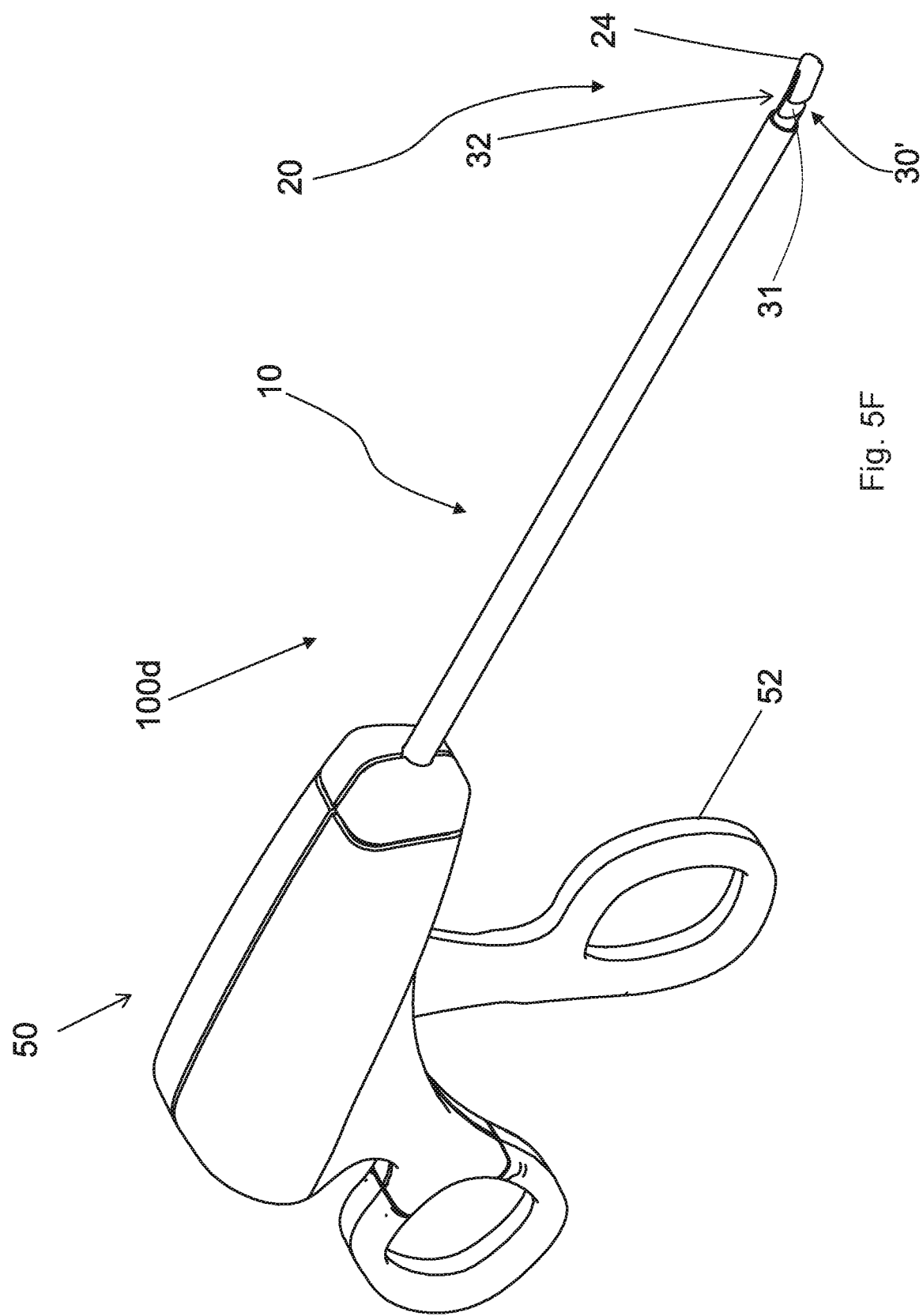
FIG. 5F illustrates a suture cutter to facilitate left-handed use accordance with an alternative embodiment of the present invention.

In still additional embodiments, the inner member 20 may be provided in various configurations in order to orient the opening 30 and the slot 32 such that it allows use of the device in either a right-handed configuration or a left-handed configuration. As described earlier with reference to FIG. 1A, the device 100 has an opening 30 with the entry channel or passage 31 of the opening being positioned along the left side of the inner member 20 forming a left facing opening 30 with a left entry passage 31, which may facilitate right-handed use of the device. Alternatively, as illustrated in FIG. 5F of the present invention, a device 100d is provided that comprises an opening with the entry channel or passage 31' of the opening into the slot 32 being positioned along the right side of the inner member 20, thus providing a right facing opening 30' with a right entry passage 31' which may facilitate left-handed use of the device 100d. As such, the inner member 20 may be provided in varying configurations in order to provide various devices for cutting suture that could be used either in a left-handed configuration or a right-handed configuration, based on user preference. Thus, in some embodiments, the slot 32 comprises a right entry passage to facilitate left handed use, whereas in some embodiments the slot 32 comprises a left entry passage to facilitate right handed use.

Figure 5G:
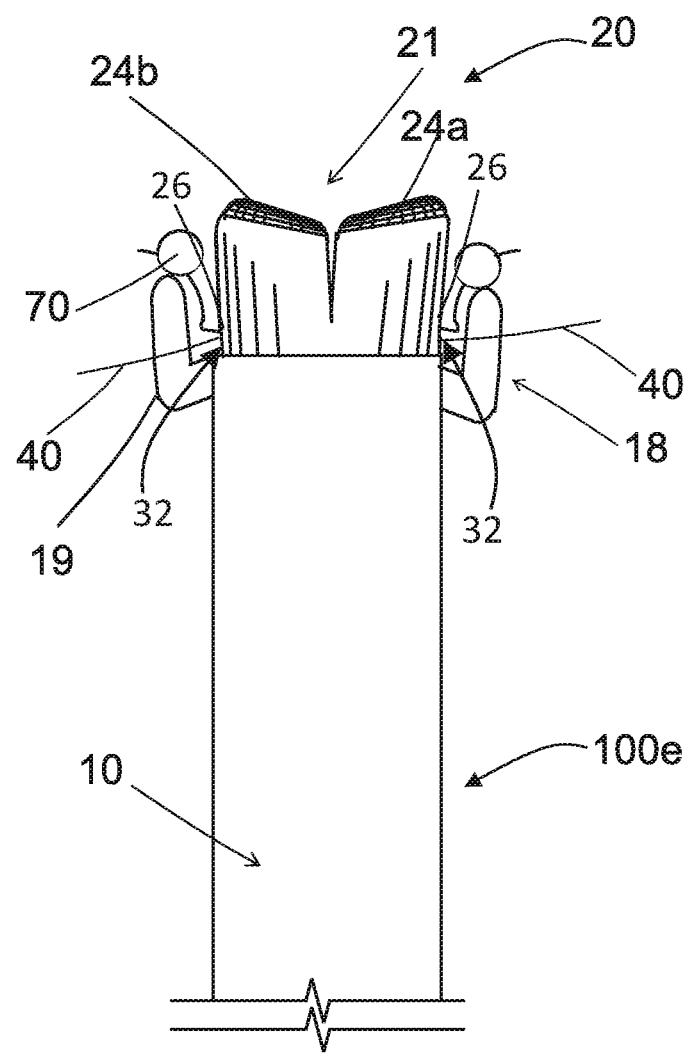
FIG. 5G illustrates a suture cutter accordance with a further alternative embodiment of the present invention.

In additional embodiments of the present invention, as shown in FIG. 5G, a device 100e is disclosed that enables cutting of suture on both sides of the inner member 20 allowing the device to be used in either the upright or nominal configuration or an upside-down configuration. The device 100e comprises a slot 32 and opening 30 along each of the opposing lateral sides of the inner member 20, within two opposing halves 24a and 24b of the distal tip 24. Each of the two opposing halves 24a, 24b of the distal tip 24 comprising a bend 23 similar to the embodiments illustrated in FIG. 3B along the interior for example at least partially along a length of the distal tip 24 defining a gap 21. The bend 23 and the gap 21 allows each of the opposing halves to flex upon advancement of the outer member 10 to cut the suture and to prevent binding. The gap 21 is wider in the unactuated state of the device 100e. The suture can be cut on either side of the distal tip 24. As illustrated the knot 70 is deflected by the arm 18' of each of the guiding flanges 18 with the tail being defined by the length of the arm 18'. Since a cutting edge 26 is defined on each side of the distal tip 24, the suture 40 may be cut on both side of the device with a knot 70 with a tail length t being produced as well as an additional piece of suture being retained within the device 100e. In some such embodiments the device 100e may be utilized to remove a segment of tissue by a width determined by the outer diameter of the inner member 20.

Figure 5H:
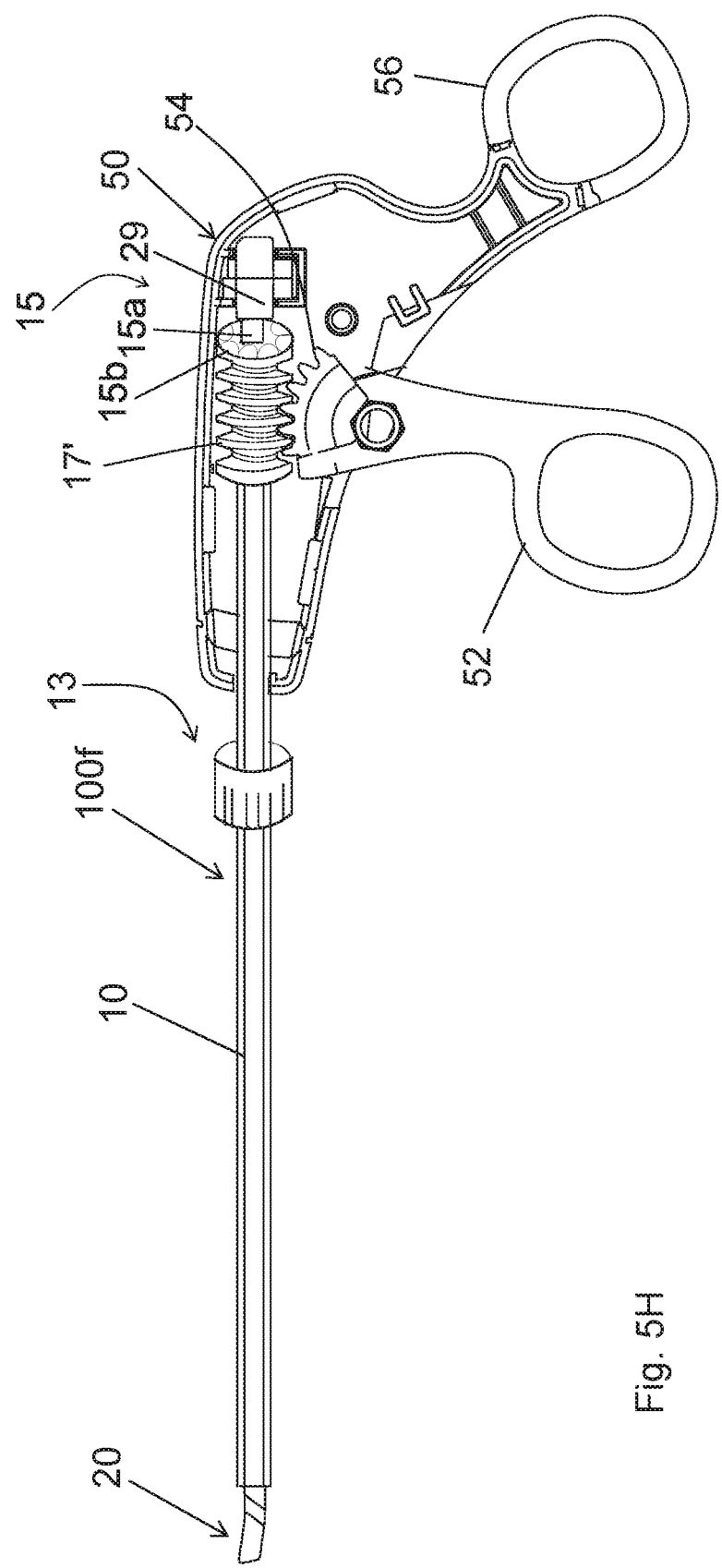
FIG. 5H illustrates a suture cutter with a feature to allow adjustable rotational configuration of one or more of the inner and outer members, accordance with an alternative embodiment of the present invention.

In some embodiments of the present invention as shown in FIG. 5H, a device 100f is shown that enables the rotational configuration of the inner and outer members 20, 10 to be adjusted in order to provide a desired cut angle. Additionally, it may allow the suture cutter to be used in a plurality of rotational configurations. In the specific example shown, the device 100f comprises a dial 13 that enables rotation of both the inner and outer members 20, 10, to enable the inner and outer members 20, 10 to achieve a desired configuration. Furthermore, the cannula or outer member hub 19 comprises a rotatable gears rack 17' to enable the rotational adjustment of the inner and outer members 20, 10. In some such embodiments both the inner and outer members 20, 10 may rotate together. Still furthermore, in some embodiments the inner member 20 may rotate independently from the outer member 10 which may not require a rotatable gears rack 17'. The device 100f is functional in a similar manner to devices described herein above. As the trigger 52 is actuated, it is pulled towards the handle grip 56 allowing advancement of the outer member 10 over the inner member 20 in order to create interference between the two at the cutting edge 26 in order to cut the suture. In some such embodiments the device 100f additionally comprises a feature for position click engagement 15 that in particular example comprises a square block 15a that creates a sound upon frictional engagement with raised ribs 15b of the rotatable gears rack 17'. In some such embodiments the position click engagement feature 15 functions to lock the rotation of the inner member 20 (and the outer member 10 in the embodiment where they are operable to rotate together) at various rotated positions.

In a further alternate embodiment of the present invention as shown in FIG. 6A and in the cross-sectional view illustrated in FIG. 6B, a device 200 is provided. The device 200 provides an inner member 20 comprising a plurality of apertures or holes that extend transversally through the inner member 20 to form tubular passages 60a, 60b and 60c that each define a channel there-through to accommodate suture in order to provide a plurality of different tail lengths. In the specific embodiment shown, the inner member 20 comprises three passages 60a, 60b and 60c that are each functional to provide a different tail length for one or more suture strands 40 that are passed there-through. Alternatively, in some embodiments the device 200 may comprises two or more tubular passages. In still other embodiments, the device 200 may comprises more than three tubular passages. In the particular example shown, each of the three tubular passages 60a, 60b and 60c define a suture entry point along a bottom surface of the inner member 20. Each of the tubular passages 60a, 60b and 60c define a respective passage length and terminate at a cutting edge 26a, 26b, 26c respectively along the top surface of the inner member 20 in order to facilitate cutting of the one or more suture strands 40. Alternatively, in some embodiments, the plurality of tubular passages may terminate at a single cutting edge 26 with the tubular passages opening into the same opening along the top portion of the inner member 20 as shown in FIG. 6C. Thus the multiple opening may meet at the same point at the cutting edge 26 whereas the suture entry points defined by openings of the tubular passages 60*a*, 60*b*, 60*c*, along the bottom portion of the inner member 20 may be different. Alternatively, the tubular passages may all open into a single opening along a bottom portion of the inner member 20 defining a single suture entry point but may exit at different points along the top portion of the inner member 20 defining multiple cutting edges. Similar to embodiments discussed previously herein above, the device 200 as shown, may facilitate cutting of strands or limbs of suture 40 that exit a knot, such as a knot 70 in order to provide a specific tail length for the cut suture strands 40. The suture strands 40 may be threaded through either of the tubular passages 60*a*, 60*b* or 60*c* such that the knot 70 rests against the bottom surface of the inner member 20. The outer member 10 may be then advanced by actuating the trigger to provide varying tail lengths as indicated by t1', t2' and t3', based on the length of the passage 60*a*, 60*b*, or 60*c*, that the suture strands 40 are passed through. Thus, in the example shown tubular passage 60*a* provides the longest tail length whereas tubular passage 60*c* provides the shortest tail length with t1'>t2'>t3'. As such, the tubular passages 60*a*, 60*b*, 60*c* allow for automatically sizing the tail length based on the suture size. For example, tubular passage 60*c* as shown is provided with a relatively small outer diameter in comparison to the remaining tubular passages 60*b*, 60*a*, in order to accommodate a relatively small diameter suture (for example suture that has a width that is less than the diameter of the tubular passage 60*c*) to provide a tail length t3' that is sufficient to prevent a small knot from unravelling. However, tubular passage 60*c* does not accommodate a relatively large diameter suture (for example suture that has a width greater than the diameter of the tubular passage 60*c*). As such, in some embodiments the tubular passage 60*c* is sized to prevent use thereof with a relatively larger diameter suture forcing the user to use one of the remaining tubular passages such as passage 60*a*. In some such embodiments as shown, such as tubular passage 60*a* may be provided with a larger outer diameter and may provide a longer channel in order to accommodate a larger suture width and the tubular passage 60*a* may facilitate creation of a relatively longer tail length t1' during use (when compared to the other passages) where the tail length t1' is of a sufficient size to prevent a larger knot from unravelling. In some examples, the device may be color coded to facilitate use of the device by allowing the user to select the appropriate tubular passage in order to cut the suture strands 40 to a desired tail length.

As such the plurality of tubular passages 60*a*, 60*b*, 60*c* may be sized to accommodate multiple sutures and may allow selective use thereof in order to allow the user to obtain a minimum tail length that is sufficient to prevent the knot from unravelling. Thus, the device 200 allows the tail length to be selected based on suture size and/or knot size.

Figure 7A:
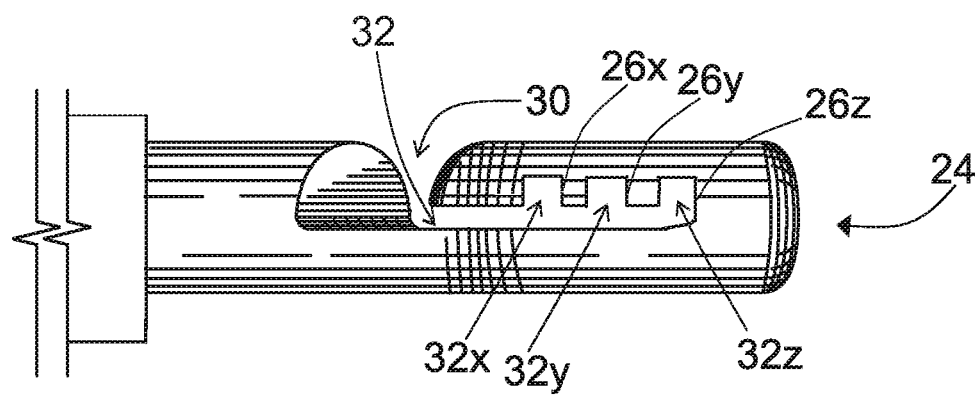
Figure 7B:
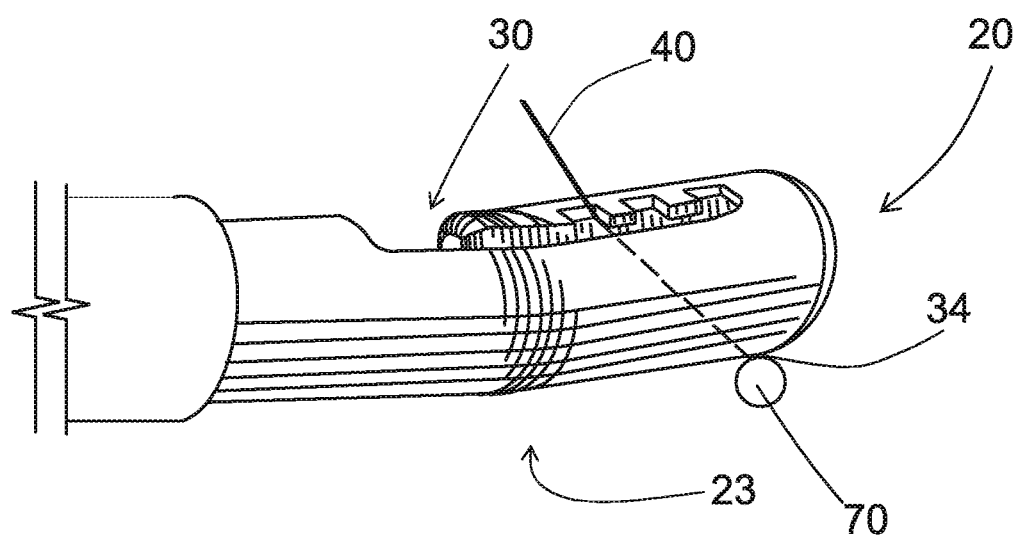

In still further embodiments of the present invention, as shown in FIGS. 7A and 7B, the device may provide multiple side grooves or side slots 32*x*, 32*y* and 32*z* that extend laterally from the slot 32 along a top portion of the inner member 20 within the distal tip 24 in order to provide multiple cutting edges 26*x*, 26*y* and 26*z* that are located at spaced apart intervals along the longitudinal length of the slot 32. Similar to embodiments discussed previously herein above, the multiple cutting edges 26*x*, 26*y*, 26*z* provide flexibility by allowing suture strands 40 to be cut with varying tail lengths. In other words the side slots 32*x*, 32*y*, 32*z* terminate at cutting edges 26*x*, 26*y*, 26*z* for example along a distal edge of each of the side slots 32*x*, 32*y*, 32*z*. The suture 40 may be placed through opening 30 within the slot 32 into one of the side slots such as side slot 32*x*, as shown in FIG. 9B, in order to facilitate cutting of the suture strand 40 at the cutting edge 26*x*. In the illustrated embodiment, side slot 32*x* is positioned furthest away from the distal tip groove 34, where the knot 70 is positioned so as to allow the maximum available tail length for the suture strand 40. Alternatively, the suture strand 40 may be positioned through side slots 32*y* and 32*z* to provide shorter tail lengths, with the side slot 32*z* being functional to provide the shortest tail length in the device configuration shown. Thus, similar to embodiments discussed herein above, side slots 32*x*, 32*y* and 32*z* provide flexibility in terms of allowing the user to cut the suture strands 40 to a desired tail length. In the illustrated embodiments, the side slots 32*x*, 32*y*, 32*z* extend along the top portion of the inner member 20 to ensure that the slot 32 remains open without ridges along the transverse length of inner member 20 within the slot 32 to ensure that the distal movement of the knot 70 is not restricted. This may facilitate placement of the knot 70 within the groove 34 against the distal surface of the inner member 20 to ensure that a desired tail length is obtained. This configuration may further reduce the risk of the knot 70 being placed proximal of the distal surface resulting in less than a desired tail length. Furthermore, as outlined herein above in FIG. 2G, the outer member 10 may have a guiding flange 18 along a distal end of the outer member 10 for example along a bottom portion thereof that function to guide and push the knot as it is advanced relative to the inner member to ensure that knot can be positioned within the groove 34 at the distal surface in order to ensure a desired tail length can be obtained.

In further embodiments of the present invention a device 100 may be provided that enables cutting of suture strands or tails emanating from a knot, where the tail length of the suture strands may be adjusted as a function of knot size. In some such examples, the groove 34 that is functional to receive a knot may be modified in order to provide a tapered configuration to facilitate automatic adjustment of the tail length based on the suture size. In one such example, as shown in FIG. 8A, the groove 34 (that opens into slot 32) comprises a tapered groove 36 that terminates at the cutting edge 26. The tapered groove 36 comprises a v-shaped configuration and functions to secure a knot of suture. More particularly, the tapered groove 36 has a wedge shaped cross-section in the transverse direction or in other words has a transverse wedge shaped cross-section. In some such examples, the tapered groove 36 may comprise a substantially elongated configuration forming an elongated tapered groove 37, as shown in FIG. 8B.

With reference now to FIG. 8C, during use a device of the present invention may be used to cut suture exiting a knot 70. In one particular example, the knot construct may be relatively large and the tapered groove 36 allows the relatively larger knot, for example knot 71, to rest against and to be wedged against a wider base portion of the tapered groove 36. This allows the knot 71 to be positioned such that a longer section of one or more suture strands 40 extend from the knot 71 till the cutting surface 26, which allows a relatively longer tail length t1 to be cut for a larger knot 71 as shown in FIG. 8E. The device 100 may be used in a similar fashion as described herein above, creating relative movement between the inner and outer member 10, 20 upon actuation of the trigger in order to cut the suture. Conversely, as shown in FIG. 8D, the tapered groove 36 allows a relatively small knot, such as knot 72, to rest against and to be wedged against a narrower portion of the tapered groove 36 which allows a relatively shorter tail length t2 to be cut for the relatively smaller knot 72, as shown in FIG. 8F. As such the tail length is defined by the distance at which the knot 70 is positioned [within the tapered groove 36 as tension is applied against the suture] from the top surface of the inner member 20 or more specifically from the cutting edge 26 of the inner member 20. In other words the tail length t is defined by the distance between the resting point of the knot 70 within the tapered groove 36 and the cutting edge 26. Thus, the device 100 for cutting suture may allow tail length t to be adjusted automatically according to the knot size. In some such embodiments, the tail length of a knot construct may be a function of the suture OD. In some such embodiments, a suture having a greater OD may result in a larger knot size which consequently may result in a longer tail length t. Similarly, a suture having a smaller OD may result in a smaller knot size which may result in a shorter tail length t. In other embodiments, the elongated tapered groove 37 as shown in FIG. 8B, may provide a similar functionality as described herein above for tapered groove 36, but may additionally offer a wider range of tail lengths based on the suture size. In other words the elongated tapered groove 37 may be more sensitive to changes in suture size, providing varying sizes of tail length.

In alternative embodiments, a tapered groove 36' may be provided, as shown in FIG. 9C and in the cross-sectional views shown in FIG. 9B and FIG. 9C that comprises a wedge shaped cross-section in the longitudinal direction or in other words comprises a longitudinal wedge shaped cross-section. Similar to the embodiments described herein above, tapered groove 36' also functions to secure a knot of suture. The tapered groove 36' functions in a similar manner as described herein below with reference to tapered groove 36 to automatically adjust the tail length based on knot size or additionally the suture size with the size of the tail length t being determined by the distance of the knot 70 from the cutting edge 26 while it is positioned within the elongated tapered groove 36' In other words the tail length t is equal to the distance between the point at which the knot 70 rests within the elongated groove 36' [as it is kept in tension so that an upwards force is exerted against it] and the cutting edge 26.

In alternate embodiments of the present invention a modified slot 32' may be provided. In one such embodiment, as shown in FIG. 9C, the inner member 20 comprises a tapered groove that comprises a conical shape. More specifically, a conical opening or conical groove 38 is provided at a distal end of the inner member 20 adjacent the cutting edge 26. In other words the conical opening 38 terminates at the cutting edge 26. The modified slot 32' provides a wedge shaped cross-section both in the longitudinal direction and the transverse direction. In other words the conical opening defines a wedge shaped cross-section along a cross-section taken along any plane along a vertical axis that that intersects the conical opening 38. The conical opening allows larger knots such as knot 71 to rest against or adjacent the base 38a of the conical opening as shown in FIG. 9A, which automatically provides a longer tail length t1 for relatively large knots, such as knot 71 as shown. Whereas, knots with a relatively smaller size such as knot 72 as shown in FIG. 9B, are able to travel further within the conical opening 38 as their movement is not impeded by the inner walls of the conical opening 38. As such the knot 72 rests adjacent the top portion of the conical opening 38 with the distance between the distal cutting edge 26 and the knot 72 being relatively short providing a shorter tail length t2. Thus, the conical opening 38 similar to tapered grooves 36, 36', 37 described herein above defines a tail length t that is equal to the distance between the resting point of the knot 70 within the conical opening 38 and the cutting edge 26 as the suture is under tension.

In still further embodiments of the present invention, as shown in FIG. 10B, an inner member 20 is provided comprising a distal tip 24 where the slot 32 along the bottom of the inner member 20 extends longitudinally defining a v-shaped tapered bottom opening or slot 34'. In some embodiments, the v-shaped tapered slot or opening 34' extends along the bottom while the remaining portions of the slot 32 have a width equal to the wider portion of the v-shaped slot 34'. During use, a knot may be positioned below the inner member 20 such that suture is routed through the entry channel or passage 31 into the longitudinally extending tapered opening 34'. The tapered opening 34' narrows towards the distal face 25 with the wider portion of the opening being defined adjacent passage 31. As such, the tapered opening 34' allows suture of varying widths or outer diameters to be held along different portions of the tapered opening 34' along its length. More specifically, the geometry of the longitudinally extending tapered opening 34' allows a suture 40 with a relatively larger suture size, for example suture 40b (which has an outer diameter that is greater than the outer diameter of suture 40a) to be held in a wider portion of opening 34' allowing a relatively longer tail length as shown by t1 in FIG. 10A. Providing a larger suture with a longer tail length may help prevent unravelling of a knot construct from the suture. The longitudinally extending opening 34' further allows a suture 40 with a relatively small suture size 40a to be held in a narrow portion of the thereof providing a relatively shorter tail length t2, as shown in FIG. 10A. Thus, the longitudinally extending opening 34' allows the thinner suture to be pushed in further allows a shorter tail length t2. As such the suture tail length can be automated based on the suture size. Thus, the embodiment illustrated in FIGS. 10A-10B, provide flexibility in terms of allowing the user to cut the suture strands 40 to a desired tail length.

In further embodiments of the present invention, as shown in FIG. 11, an outer member 10 may be provided that comprises an inner or leading edge 14 that comprises a bevel edge 16 that defines a cutting edge to facilitate cutting of the suture upon advancement of the outer member 10 over the inner member 20. The bevel edge 16 may aid in cutting through thicker or tougher suture material. In some such embodiments the bevel edge 16 may have serrations along the edge in order to facilitate cutting of the suture.

In still a further embodiment of the present invention, the inner member 20 comprises a removable or replaceable distal tip 24', as shown in FIG. 12A which allows the distal tip 24' to be replaced as desired. In some such embodiments, a plurality of removable distal tips 24' may be provided with each being customized to provide a desired tail length and each may be independently mounted or coupled to a proximal shaft portion of the inner member 20. In alternate embodiments, a plurality of removable distal tips 24' may be provided, with each distal tip 24' being customized to optimize cutting of a suture of a particular selected size. In still other embodiments, the removable distal tip 24' may be selected based on the suture size in order to obtain a desired tail length for the suture. As such, the removable distal tip 24' is detachably coupled to the proximal shaft portion of the inner member 20 (which is the portion of the inner member 20 that is separate from the distal tip 24'). In the specific example shown, the distal tip 24' may be threadably coupled to a proximal shaft portion of the inner member 20. In a specific instance of this example, the removable distal tip 24' comprises an externally threaded member 74 that is operable to engage inner threads with the proximal shaft portion of the inner member 20 to allow the distal tip 24' to be coupled to the inner member 20.

In still further embodiments of the present invention, as shown in FIGS. 12B and 12C the outer member 10 may comprises a removable or replaceable distal end or distal portion 10a that is detachably coupled to a proximal shaft portion 10b of the outer member 10. In the illustrated example shown, the replaceable distal end 10a is threadably coupled to the shaft portion 10b of the outer member 10. More specifically, the replaceable distal end 10a comprises an externally threaded section 76 that is operable to threadably engage an internally threaded section 77 of the shaft portion 10b of the outer member 10. The replaceable distal end 10a may be replaced after several uses. In some such embodiments, the inner member 20 also comprises a removable distal tip 24' that is detachably coupled to a proximal shaft portion of the inner member 20. The removable distal tip 24' of the inner member 20 may be coupled to the shaft portion of the inner member 20 after the replaceable distal end 10a of the outer member 10 has been coupled to the proximal shaft portion 10b of the outer member to facilitate assembly of the device so that the bend 23 of the removable distal tip 24' of the inner member 20 does not hinder assembly of the outer member 10. Furthermore, in some such embodiments, the replaceable distal end 10a may sterilizable after use in order to enable re-use. In some such embodiments, the replaceable distal end may comprise a biocompatible material that allows it to be sterilized. In one such example the replaceable distal end 10a comprises metallic components. In a specific example of this the inner member 20 including such as medical grade stainless steel.

In the embodiment described herein the outer member 10 is defined as 'solid' once the components namely the replaceable distal end 10a and the shaft portion 10b of the outer member are connected or coupled to one another.

In an additional embodiment of the present invention as shown in FIG. 13A, the inner member 20, the inner member comprises a distal tip 24 where the slot 32 is enclosed forming an enclosed slot 33 defining opening 35 therethrough, and that terminates in a distal cutting edge 26. The enclosed slot 33 defines a locking feature 85 to prevent premature cutting of suture by allowing suture 40 to be threaded through the opening 35 such that is retained within the opening 35. Thus, when the trigger is actuated on device 100 to allow relative movement between the inner and outer members 20, 10 in order to cut the suture the suture 40 remains held within the opening 35 allowing the outer member 10 to be advanced over the inner member 20 to create an interference there-between at the cutting edge 26 in order to cut the suture.

In additional embodiments of the present invention, as shown in FIG. 13B, and cross-sectional views shown in FIGS. 13C and 13D, a feature or control feature is provided in order to provide controlled actuation of the trigger to allow the suture to be held within the device during device advancement up to the knot while preventing accidental cutting of the suture during advancement. In some such embodiments the device comprises a locking feature to allow the suture to be locked within the slot 32 during device or instrument advancement by allowing partial actuation of the trigger to allow advancement of the outer member 10 to enclose the suture within the slot 32 but preventing further actuation of the trigger to prevent premature cutting of the suture. In some such embodiments, a resistive force is provided between the inner and outer members 20, 10 as they are being actuated in order to impede their movement after partial actuation of the trigger. For example, as shown in FIGS. 13B, 13C and 13D, a locking feature 85 is provided, which in some embodiments comprises an interference fit arrangement 86 comprising a projection 80 on the inner member 20 that is received within an aperture 82 of the outer member 10.

During use, as the trigger is actuated the outer member 10 advanced over the inner member 20 such that the projection 80 engages the aperture 82 of the outer member 10 which provides a locking function to effectively lock the inner and outer members 20, 10 together, as illustrated in FIG. 13D. The locking feature 85 impedes the movement of the outer member 10 and prevents the outer member 10 from being advanced past the opening 30 of the inner member 20 [Similar to the position shown in FIG. 4B] thus securing the suture within the slot 32. As such, the locking feature 85 enables the device to be actuated partially into a locked configuration such that the outer member 10, 20 is advanced half-way towards its final cutting position (position at which the suture is cut). Thus the locking feature 85 is operable to engage upon partial actuation of the trigger in order to impede further actuation of the trigger and prevents the suture from being cut until the device has been fully advanced to a knot for example at a desired site within the patient's body. Additional force is then required to overcome the resistance created by the locking feature 85 in order to fully actuate the trigger in order to complete the necessary relative motion between the inner and outer members 20, 10 in order to cut the suture. Therefore, the locking feature 85 provides controlled actuation of the trigger in order to allow the device to be advanced to till the knot white retaining the suture within the device and preventing the suture from being cut prematurely.

In alternate embodiments, the device may be equipped with a spring which may force the user to provide extra force after the trigger has been actuated partially in order to complete the actuation in order to cut the suture 40. As such, some embodiments of the present invention provide a mechanism to retain the suture within the slot 32 during advancement of the device while preventing premature cutting of the suture. The locking feature 85 ensures that the suture is cut once the device is positioned at the knot to at the cutting edge 26 and may allow the desired tail length to be obtained. In alternate embodiments, the interference fit arrangement 85 may comprise a projection on the outer member 10 that is configured to engage an aperture within the inner member 20.

In additional embodiments of the present invention, as shown in FIGS. 13E and 13F, a locking feature 85 may be provided in the form of an interference fit arrangement 86 that is formed between a projection or detent 83 on the cannula hub 19 of the outer member 10 and a recess 84 formed within the handle housing 50. In the initial position within the handle housing 50 prior to actuation, the hub 19 is positioned within the housing 50 such that it is free to move upon actuation of the trigger, as shown in FIG. 13E. Once the trigger is actuated the hub advances until the detent 83 reaches the recess 84 and is operable to engage therewith so that it is held therein preventing further actuation of the trigger, as shown in FIG. 13F. As shown, the locking feature 85 allows the trigger to be actuated partially until the outer member 10 is advanced over the inner member 20 to secure the suture 40 within the slot 32. In order to facilitate further actuation of the trigger in order to advance the cannula hub 19, the recess 84 provides a bevel interface 84'. As the trigger is advanced further the detent 83 rides against the bevel interface 84' to exit the recess 84 allowing the trigger to be actuated fully in order to advance the outer member 10 to cut the suture.

In additional embodiments of the present invention as shown in FIG. 14, the locking feature comprises a locking ramp 86 that is coupled to the trigger 52 that functions to limit the actuation of the trigger so that the trigger is pulled only partially. The locking ramp extends along a bar 86' that is coupled to the trigger 52. The bar 86' is moveable within the handle housing 50 upon actuation of the trigger 52 until the locking ramp 86 prevents its further movement into the handle housing 50. For example the locking ramp 86 enables the trigger 52 to be advanced halfway to enable the outer member 10 to be advanced to cover the opening 30 to lock the suture within the slot 32 but impedes further actuation of the trigger. A mechanism may then be provided to allow further advancement of the outer member 10 to enable interaction between the inner and outer members 20, 10 in order to cut the suture. In one particular example as shown the locking ramp 86 may be depressed to enable continued advancement of the trigger 52 by allowing the bar 86' to travel further the handle housing 50.

In some embodiments of the present invention, the device of the present invention may be used to cut a plurality of different sutures such as multi-filament and single strand sutures. In some examples of multi-filament sutures, the multi-filament suture may comprise a single braid. Alternatively, the multi-filament suture may comprise a braid surrounding an un-braided core. In some such examples, polydiaxanone may be used as an outer braid to support a non-absorbable core. In some embodiments, the suture may comprise non-absorbable sutures, which in some examples may comprise polyester or polyethylene (frequently ultra-high molecular weight polyethylene, or UHMWPE) or Nylon. In other embodiments, the suture may comprise an absorbable compound such as polydiaxanone. In other embodiments, the device of the present invention may be used to cut single strand or monofilament sutures as mentioned previously. In some examples, the monofilament suture comprises UHMPWE. In some instances of the present invention, the device may be used to cut suture that is used in orthopaedic procedures. In some embodiments the device of the present invention may be used to cut suture comprising for example:

Ethibond, a polyester braid with polyester core; FiberWire, a ultra-high molecular weight polyethylene (UHMWPE) core with a polyester and UHWMPE braided jacket; Force Fiber, UHMPWE braid wire without an inner core; UHWMPE braid such as Herculine, HiFi, Magnum Wire, MaxBraid; Orthocord, a polyblend with partially-absorbing polydiaxanone; PDS II, a polydioxanone monofilament that is absorbable; Surgilon, 6 and 6.6 Nylon multifilament braids; Ultrabraid, a polyethylene braid. In still other embodiments, the device of the present invention may be used 2 non-absorbable braided sutures of size 3-0 connected with a loop of green PET suture of size 2-0, which is used to tighten the suture assemblies together.

In some embodiments, a device of the present invention may be used to cut tissue within a patient's body. In some such embodiments, a device of the present invention may be used to cut various tissues such as ligaments, tendons and blood vessels. In other embodiments, a device of the present invention may be usable to cut any other tissue within a patient's body.

In one broad aspect, embodiments of the present invention comprise a suture cutter comprising: a solid outer member defining a lumen there-through; an inner member received at least partially within the lumen, a portion of the inner member defining a curve, the inner member further defining a feature for retaining a strand of suture; and at least one of the inner and outer members being moveable with respect to the other of the inner and outer members for cutting the strand of suture.

In a further broad aspect, embodiments of the present invention comprise a suture cutter comprising: an outer member defining a lumen there-through; an inner member received at least partially within the lumen, the inner member defining a curve, the inner member defining a feature for retaining a strand of suture; the inner member being configured to have an offset-to-diameter ratio of between about 1.1 and about 1.3; and at least one of the inner and outer members being moveable with respect to the other of the inner and outer members to for cutting the strand of suture.

In still a further broad aspect, embodiments of the present invention comprise a suture cutter comprising: an outer member defining a lumen there-through; and an inner member received at least partially within the lumen, a portion of the inner member defining a curve, the inner member further defining a feature for retaining a strand of suture; at least one of the inner and outer members being moveable with respect to the other of the inner and outer members for cutting the strand of suture; and the inner member being deflectable upon movement of the at least one of the inner and outer members with a deflection to baseline value of between about 15% to about 33%.

In another broad aspect, embodiments of the present invention comprise a suture cutter comprising: an outer member defining a lumen there-through; and an inner member at least partially received within the lumen, the inner member defining a curve, the inner member further defining a feature for retaining a strand of suture; at least one of the inner and outer members being moveable with respect to the other of the inner and outer members for cutting the strand of suture; and the outer member being deflectable upon movement of the at least one of the inner and outer members with a deflection to baseline value of less than about 85%.

In still another broad aspect, embodiments of the present invention comprise a suture cutter comprising: an outer member defining a lumen there-through; and an inner member at least partially received within the lumen, the inner member defining a curve, the inner member further defining a feature for retaining a strand of suture, the feature defining a cutting edge that is vertically offset by a distance of between about 0.012" to about 0.026" from a longitudinal axis extending along a top edge of the inner member; at least one of the inner and outer members being moveable with respect to the other of the inner and outer members for cutting the strand of suture; and each of the inner and outer members being deflectable upon movement of the at least one of the inner and outer members, with a cumulative deflection of both the inner and the outer members being approximately equivalent to the offset distance.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A suture cutter comprising:
a solid outer member defining a lumen there-through, the solid outer member defining a longitudinal axis, and the solid outer member having a side-wall without a cut-out;
an inner member received partially within the lumen, the inner member comprising a distal portion wherein the distal portion is offset from the longitudinal axis and defines a curve, the inner member further comprising a feature for retaining a strand of suture;
at least one of the inner and outer members being moveable with respect to the other of the inner and outer members for cutting the strand of suture; and
whereby when the outer member is advanced over the inner member, the distal portion of the inner member is biased against the outer member, thereby creating a cutting mechanism for cutting the strand of suture.

2. The suture cutter of claim 1, wherein the inner member comprises a solid shaft.

3. The suture cutter of claim 1, further comprising a trigger for moving the at least one of the inner and outer members.

4. The suture cutter of claim 3, wherein the trigger is actuatable by a predetermined maximum amount to prevent binding of the suture cutter.

5. The suture cutter of claim 3, further comprising a control feature to enable controlled actuation of the trigger.

6. The suture cutter of claim 1, wherein the outer member is moveable distally with respect to the inner member.

7. The suture cutter of claim 1, wherein the feature comprises a slot formed within the distal portion of the inner member, a distal end of the slot defining a cutting edge.

8. The suture cutter of claim 7, wherein the cutting edge is offset by between about 0.012" to about 0.026" from a longitudinal axis extending along a top edge of the inner member, to prevent the suture cutter from binding.

9. The suture cutter of claim 7, wherein the curve defines a curvature of between about 6 degrees to about 8 degrees relative to a longitudinal axis of the inner member.

10. The suture cutter of claim 7, wherein the slot comprises a side loading slot for loading the suture into the suture cutter.

11. The suture cutter of claim 7, wherein the slot defines an inside edge having an inside edge length, whereby a tail length of a cut strand of suture is substantially equivalent to the inside edge length.

12. The suture cutter of claim 11, wherein a bottom portion of the slot terminates at a distal groove for retaining a knot formed from the strand of suture.

13. The suture cutter of claim 7, wherein a distal end of the outer member defines a leading edge, for creating interference between an inner surface of the outer member at the leading edge and the cutting edge of the inner member in order to cut the strand of suture held there-between upon movement of the outer member over the inner member.

14. The suture cutter of claim 1, wherein the inner member has a deflection to base-line value of between about 15% to about 33%.

15. The suture cutter of claim 7, wherein the inner member comprises a feature for adjusting a tail length of a cut strand of suture based on an outer diameter of the suture.

16. The suture cutter of claim 15, wherein the feature allows for automatically adjusting the tail length based on a size of a knot formed from the strand of suture.

17. The suture cutter of claim 16, wherein the feature comprises a tapered groove for securing a knot formed from the strand of suture, wherein the tail length is determined by a distance between a resting point of a knot within the tapered groove and the cutting edge.

18. The suture cutter of claim 17, wherein the tapered groove terminates at the cutting edge.

19. The suture cutter of claim 1, wherein outer member comprises a leading edge defining a bevel edge to facilitate cutting of the suture upon relative movement between the outer member and the inner member.

20. The suture cutter of claim 1, wherein the inner member is configured to have an offset-to-diameter ratio of between about 1.1 to about 1.3.

21. The suture cutter of claim 1, wherein the cutting mechanism is operable to cut the strand of suture by the interference between the distal portion of the inner member and an inner surface of the outer member to create a shearing force.

* * * * *